United States Patent
Totary-Jain

(10) Patent No.: US 12,012,637 B2
(45) Date of Patent: Jun. 18, 2024

(54) METHODS FOR DETECTING AND TREATING PROPRANOLOL SENSITIVE TUMORS

(71) Applicant: University of South Florida, Tampa, FL (US)

(72) Inventor: Hana Totary-Jain, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 44 days.

(21) Appl. No.: 17/513,279

(22) Filed: Oct. 28, 2021

(65) Prior Publication Data

US 2022/0049319 A1    Feb. 17, 2022

Related U.S. Application Data

(63) Continuation of application No. 16/183,025, filed on Nov. 7, 2018, now abandoned.

(60) Provisional application No. 62/582,506, filed on Nov. 7, 2017.

(51) Int. Cl.
    *C12Q 1/6886*    (2018.01)

(52) U.S. Cl.
    CPC ..... *C12Q 1/6886* (2013.01); *C12Q 2600/106* (2013.01); *C12Q 2600/158* (2013.01); *C12Q 2600/178* (2013.01)

(58) Field of Classification Search
    None
    See application file for complete search history.

(56) References Cited

U.S. PATENT DOCUMENTS

2015/0301060 A1    10/2015    Gerner et al.
2017/0234884 A1    8/2017     Baillie et al.

FOREIGN PATENT DOCUMENTS

EP    2187878    6/2011

OTHER PUBLICATIONS

Wang et al Carcinogenesis. 31(9): 1516-1522 (Year: 2010).*
Choi, Seung Ah, et al. "LIN28B is highly expressed in atypical teratoid/rhabdoid tumor (AT/RT) and suppressed through the restoration of SMARCB1." Cancer cell international 16.1 (2016): 1-10.
Canfield, John, et al. "Decreased LIN28B in preeclampsia impairs human trophoblast differentiation and migration." The FASEB Journal 33.2 (2019): 2759-2769.
NCBI Database GenBank Association No. NM 024674.4, Mar. 15, 2015.
Rodini, Carolina Oliveira, et al. "Expression analysis of stem cell-related genes reveal OCT4 as a predictor of poor clinical outcome in medulloblastoma." Journal of neuro-oncology 106.1 (2012): 71-79.
Mong, Ezinne Francess, et al. "Modulation of LIN28B/Let-7 Signaling by Propranolol Contributes to Infantile Hemangioma Involution." Arteriosclerosis, thrombosis, and vascular biology38.6 (2018): 1321-1332.
Poster. LIN28B/let-7 axis correlates with infantile hemangioma stages and response to propranolol, 2018, Mong et al. USF Health. Feb. 2018.
Moore, John C. "The Role and Regulation of Etv2 in Zebrafish Vascular Development: A Dissertation." (2013), 204 pages.
Tu, Jun-Bo, et al. "Induction of apoptosis in infantile hemangioma endothelial cells by propranolol." Experimental and therapeutic medicine 6.2 (2013): 574-578.
Balzeau, Julien, et al. "The LIN28/let-7 pathway in cancer." Frontiers in genetics 8 (2017): 31.
Smith CJ, Friedlander SF, Guma M, Kavanaugh A, Chambers CD. Infantile hemangiomas: An updated review on risk factors, pathogenesis, and treatment. Birth Defects Res. 2017; 109:809-815.
Darrow DH, Greene AK, Mancini AJ, Nopper AJ, Section on Dermatology SOO-H, Neck S, Section on Plastic S. Diagnosis and management of infantile hemangioma: Executive summary. Pediatrics. 2015;136:786-791.
Greenberger S, Bischoff J. Pathogenesis of infantile haemangioma. Br J Dermatol. 2013;169:12-19.
North PE, Waner M, Mizeracki A, Mihm MC, Jr. Glut1: A newly discovered immunohistochemical marker for juvenile hemangiomas. Hum Pathol. 2000;31:11-22.
Mulliken JB, Glowacki J. Hemangiomas and vascular malformations in infants and children: A classification based on endothelial characteristics. Plast Reconstr Surg. 1982;69:412-422.
Amaya CN, Bryan BA. Enrichment of the embryonic stem cell reprogramming factors oct4, nanog, myc, and sox2 in benign and malignant vascular tumors. BMC Clin Pathol. 2015;15:18.
Strub GM, Kirsh AL, Whipple ME, Kuo WP, Keller RB, Kapur RP, Majesky MW, Perkins JA. Endothelial and circulating c19mc micrornas are biomarkers of infantile hemangioma. JCI Insight. 2016;1:e88856.
Bentwich I, Avniel A, Karov Y, Aharonov R, Gilad S, Barad O, Barzilai A, Einat P, Einav U, Meiri E, Sharon E, Spector Y, Bentwich Z. Identification of hundreds of conserved and nonconserved human micrornas. Nat Genet. 2005;37:766-770.
Kleinman CL, Gerges N, Papillon-Cavanagh S et al. Fusion of TTYH1 with the c19mc microrna cluster drives expression of a brain-specific dnmt3b isoform in the embryonal brain tumor etmr. Nat Genet. 2014;46:39-44.
Morales-Prieto DM, Ospina-Prieto S, Chaiwangyen W, Schoenleben M, Markert UR. Pregnancy-associated mirna-clusters. J Reprod Immunol. 2013;97:51-61.
Li M, Lee KF, Lu Y, Clarke I et al. Frequent amplification of a chr19q13.41 microrna polycistron in aggressive primitive neuroectodermal brain tumors. Cancer Cell. 2009;16:533-546.
Barnes CM, Huang S, Kaipainen A, Sanoudou D, Chen EJ, Eichler GS, Guo Y, Yu Y, Ingber DE, Mulliken JB, Beggs AH, Folkman J, Fishman SJ. Evidence by molecular profiling for a placental origin of infantile hemangioma. Proc Natl Acad Sci U S A. 2005;102:19097-19102.

(Continued)

*Primary Examiner* — Carla J Myers
(74) *Attorney, Agent, or Firm* — Meunier Carlin & Curfman LLC

(57) ABSTRACT

The present disclosure relates to methods for detecting and treating propranolol sensitive tumors.

7 Claims, 4 Drawing Sheets

Specification includes a Sequence Listing.

(56) References Cited

OTHER PUBLICATIONS

North PE, Waner M, Mizeracki A, Mrak RE, Nicholas R, Kincannon J, Suen JY, Mihm MC, Jr. A unique microvascular phenotype shared by juvenile hemangiomas and human placenta. Arch Dermatol. 2001;137:559-570.

Khan ZA, Boscolo E, Picard A, Psutka S, Melero-Martin JM, Bartch TC, Mulliken JB, Bischoff J. Multipotential stem cells recapitulate human infantile hemangioma in immunodeficient mice. J Clin Invest. 2008;118:2592-2599.

Huang L, Nakayama H, Klagsbrun M, Mulliken JB, Bischoff J. Glucose transporter 1-positive endothelial cells in infantile hemangioma exhibit features of facultative stem cells. Stem Cells. 2015;33:133-145.

Leaute-Labreze C, Dumas de la Roque E, Hubiche T, Boralevi F, Thambo JB, Taieb A. Propranolol for severe hemangiomas of infancy. N Engl J Med. 2008;358:2649-2651.

Leaute-Labreze C, Hoeger P, Mazereeuw-Hautier J, et al. A randomized, controlled trial of oral propranolol in infantile hemangioma. N Engl J Med. 2015;372:735-746.

Heo I, Joo C, Cho J, Ha M, Han J, Kim VN. Lin28 mediates the terminal uridylation of let-7 precursor microrna. Mol Cell. 2008;32:276-284.

Viswanathan SR, Daley GQ, Gregory RI. Selective blockade of microrna processing by lin28. Science. 2008;320:97-100.

Reinhart BJ, Slack FJ, Basson M, Pasquinelli AE, Bettinger JC, Rougvie AE, Horvitz HR, Ruvkun G. The 21-nucleotide let-7 rna regulates developmental timing in caenorhabditis elegans. Nature. 2000;403:901-906.

Takahashi K, Yamanaka S. Induction of pluripotent stem cells from mouse embryonic and adult fibroblast cultures by defined factors. Cell. 2006;126:663-676.

Yu J, Vodyanik MA, Smuga-Otto K, Antosiewicz-Bourget J, Frane JL, Tian S, Nie J, Jonsdottir GA, Ruotti V, Stewart R, Slukvin, II, Thomson JA. Induced pluripotent stem cell lines derived from human somatic cells. Science. 2007;318:1917-1920.

Zhang J, Ratanasirintrawoot S, Chandrasekaran S, et al. Lin28 regulates stem cell metabolism and conversion to primed pluripotency. Cell Stem Cell. 2016;19:66-80.

Kalluri R, Weinberg RA. The basics of epithelial-mesenchymal transition. J Clin Invest. 2009;119:1420-1428.

Gonzalez DM, Medici D. Signaling mechanisms of the epithelial-mesenchymal transition. Science Signaling. 2014;7(344):re8.

Li RH, Liang JL, Ni S, Zhou T, et al. A mesenchymal-to-epithelial transition initiates and is required for the nuclear reprogramming of mouse fibroblasts. Cell Stem Cell. 2010;7:51-63.

Munabi NC, England RW, Edwards AK, Kitajewski AA, Tan QK, Weinstein A, Kung JE, Wilcox M, Kitajewski JK, Shawber CJ, Wu JK. Propranolol targets hemangioma stem cells via camp and mitogen-activated protein kinase regulation. Stem Cells Transl Med. 2016;5:45-55.

Khan ZA, Melero-Martin JM, Wu X, Paruchuri S, Boscolo E, Mulliken JB, Bischoff J. Endothelial progenitor cells from infantile hemangioma and umbilical cord blood display unique cellular responses to endostatin. Blood. 2006; 108:915-921.

Santulli G, Wronska A, Uryu K, Diacovo TG, Gao M, Marx SO, Kitajewski J, Chilton JM, Akat KM, Tuschl T, Marks AR, Totary-Jain H. A selective microrna-based strategy inhibits restenosis while preserving endothelial function. J Clin Invest. 2014; 124:4102-4114.

Noguer-Dance M, Abu-Amero S, Al-Khtib M, Lefevre A, Coullin P, Moore GE, Cavaille J. The primate-specific microrna gene cluster (c19mc) is imprinted in the placenta. Hum Mol Genet. 2010;19:3566-3582.

Totary-Jain H, Sanoudou D, Ben-Dov IZ, Dautriche CN, Guarnieri P, Marx SO, Tuschl T, Marks AR. Reprogramming of the microrna transcriptome mediates resistance to rapamycin. J Biol Chem. 2013;288:6034-6044.

Guo JU, Su Y, Zhong C, Ming GL, Song H. Hydroxylation of 5-methylcytosine by tet1 promotes active DNA demethylation in the adult brain. Cell. 2011;145:423-434.

Jensen EC. Quantitative analysis of histological staining and fluorescence using imageJ. Anatomical Record-Advances in Integrative Anatomy and Evolutionary Biology. 2013;296:378-381.

Totary-Jain H, Sanoudou D, Dautriche CN, Schneller H, Zambrana L, Marks AR. Rapamycin resistance is linked to defective regulation of skp2. Cancer Res. 2012;72:1836-1843.

Hafner M, Renwick N, Farazi TA, Mihailovic A, Pena JT, Tuschl T. Barcoded cdna library preparation for small rna profiling by next-generation sequencing. Methods. 2012;58:164-170.

Farazi TA, Brown M, Morozov P, Ten Hoeve JJ, Ben-Dov IZ, Hovestadt V, Hafner M, Renwick N, Mihailovic A, Wessels LF, Tuschl T. Bioinformatic analysis of barcoded cdna libraries for small rna profiling by next-generation sequencing. Methods. 2012;58:171-187.

Brown M, Suryawanshi H, Hafner M, Farazi TA, Tuschl T. Mammalian mirna curation through next-generation sequencing. Front Genet. 2013;4:145.

Farazi TA, Horlings HM, Ten Hoeve JJ, et al. Microrna sequence and expression analysis in breast tumors by deep sequencing. Cancer Res. 2011;71:4443-4453.

Akat KM, Moore-McGriff D, Morozova P, Browna M, Gogakos T, Da Rosa JC, Mihailovic A, Sauer M, Ji RP, Ramarathnam A, Totary-Jain H, Williams Z, Tuschl T, Schulze PC. Comparative rna-sequencing analysis of myocardial and circulating small rnas in human heart failure and their utility as biomarkers. Proceedings of the National Academy of Sciences of the United States of America. 2014; 111:11151-11156.

Dobin A, Davis CA, Schlesinger F, Drenkow J, Zaleski C, Jha S, Batut P, Chaisson M, Gingeras TR. Star: Ultrafast universal rna-seq aligner. Bioinformatics. 2013;29:15-21.

Harbi S, Wang R, Gregory M, Hanson N, Kobylarz K, Ryan K, Deng Y, Lopez P, Chiriboga L, Mignatti P. Infantile hemangioma originates from a dysregulated but not fully transformed multipotent stem cell. Sci Rep. 2016;6:35811.

Heo I, Joo C, Kim YK, Ha M, Yoon MJ, Cho J, Yeom KH, Han J, Kim VN. Tut4 in concert with lin28 suppresses microrna biogenesis through pre-microrna uridylation. Cell. 2009;138:696-708.

Rybak A, Fuchs H, Smirnova L, Brandt C, Pohl EE, Nitsch R, Wulczyn FG. A feedback loop comprising lin-28 and let-7 controls pre-let-7 maturation during neural stem-cell commitment. Nat Cell Biol. 2008;10:987-993.

Nguyen PN, Huang CJ, Sugii S, Cheong SK, Choo KB. Selective activation of mirnas of the primate-specific chromosome 19 mirna cluster (c19mc) in cancer and stem cells and possible contribution to regulation of apoptosis. J Biomed Sci. 2017;24:20.

Laurent LC, Chen J, Ulitsky I, Mueller FJ, Lu C, Shamir R, Fan JB, Loring JF. Comprehensive microrna profiling reveals a unique human embryonic stem cell signature dominated by a single seed sequence. Stem cells. 2008;26:1506-1516.

Bar M, Wyman SK, Fritz BR, et al. Microrna discovery and profiling in human embryonic stem cells by deep sequencing of small rna libraries. Stem cells. 2008;26:2496-2505.

Edwards AK, Glithero K, Grzesik P, Kitajewski AA, Munabi NC, Hardy K, Tan QK, Schonning M, Kangsamaksin T, Kitajewski JK, Shawber CJ, Wu JK. Notch3 regulates stem-to-mural cell differentiation in infantile hemangioma. JCI Insight. 2017;2.

Cotterman R, Knoepfler PS. N-myc regulates expression of pluripotency genes in neuroblastoma including lif, klf2, klf4, and lin28b. PLoS One. 2009;4:e5799.

Beckers A, Van Peer G, Carter DR, et al. Mycn-driven regulatory mechanisms controlling lin28b in neuroblastoma. Cancer Lett. 2015;366:123-132.

Shyh-Chang N, Daley GQ. Lin28: Primal regulator of growth and metabolism in stem cells. Cell Stem Cell. 2013;12:395-406.

Hafner M, Max KE, Bandaru P, Morozov P, Gerstberger S, Brown M, Molina H, Tuschl T. Identification of mrnas bound and regulated by human lin28 proteins and molecular requirements for rna recognition. RNA. 2013;19:613-626.

Louis DN, Perry A, Reifenberger G, von Deimling A, Figarella-Branger D, Cavenee WK, Ohgaki H, Wiestler OD, Kleihues P,

(56) References Cited

OTHER PUBLICATIONS

Ellison DW. The 2016 world health organization classification of tumors of the central nervous system: A summary. Acta Neuropathol. 2016;131:803-820.

Rippe V, Dittberner L, Lorenz VN, Drieschner N, Nimzyk R, Sendt W, Junker K, Belge G, Bullerdiek J. The two stem cell microrna gene clusters c19mc and mir-371-3 are activated by specific chromosomal rearrangements in a subgroup of thyroid adenomas. PLoS One. 2010;5:e9485.

Borchert GM, Lanier W, Davidson BL. Rna polymerase iii transcribes human micrornas. Nat Struct Mol Biol. 2006;13:1097-1101.

Saito Y, Suzuki H, Tsugawa H, Nakagawa I, Matsuzaki J, Kanai Y, Hibi T. Chromatin remodeling at alu repeats by epigenetic treatment activates silenced microrna-512-5p with downregulation of mcl-1 in human gastric cancer cells. Oncogene. 2009;28:2738-2744.

Piskounova E, Polytarchou C, Thornton JE, LaPierre RJ, Pothoulakis C, Hagan JP, Iliopoulos D, Gregory RI. Lin28a and lin28b inhibit let-7 microrna biogenesis by distinct mechanisms. Cell. 2011;147:1066-1079.

Zeng Y, Yao B, Shin J, et.al. Lin28a binds active promoters and recruits tet1 to regulate gene expression. Mol Cell. 2016;61:153-160.

Wilbert ML, Huelga SC, Kapeli K, et al. Lin28 binds messenger rnas at ggaga motifs and regulates splicing factor abundance. Mol Cell. 2012;48:195-206.

Benhamed M, Herbig U, Ye T, Dejean A, Bischof O. Senescence is an endogenous trigger for microrna-directed transcriptional gene silencing in human cells. Nat Cell Biol. 2012;14:266-275.

Fritz AL, Adil MM, Mao SR, Schaffer DV. Camp and epac signaling functionally replace oct4 during induced pluripotent stem cell reprogramming. Mol Ther. 2015;23:952-963.

England RW, Hardy KL, Kitajewski AM, Wong A, Kitajewski JK, Shawber CJ, Wu JK. Propranolol promotes accelerated and dysregulated adipogenesis in hemangioma stem cells. Ann Plast Surg. 2014;73 Suppl 1:S119-124.

Ma X, Zhao T, Ouyang T, Xin S, Ma Y, Chang M. Propranolol enhanced adipogenesis instead of induction of apoptosis of hemangiomas stem cells. Int J Clin Exp Pathol. 2014;7:3809-3817.

Balzeau J, Menezes MR, Cao S, Hagan JP. The lin28/let-7 pathway in cancer. Front Genet. 2017;8:31.

Pantziarka P, Bouche G, Sukhatme V, Meheus L, Rooman I, Sukhatme VP. Repurposing drugs in oncology (redo)-propranolol as an anti-cancer agent. Ecancermedicalscience. 2016;10:680.

\* cited by examiner

METHODS FOR DETECTING AND TREATING PROPRANOLOL SENSITIVE TUMORS

CROSS REFERENCE TO RELATED APPLICATIONS

This application is a continuation of U.S. application Ser. No. 16/183,025, filed Nov. 7, 2018, which claims the benefit of U.S. Provisional Patent Application Ser. No. 62/582,506 filed Nov. 7, 2017, the disclosure of both of which are expressly incorporated herein by reference.

STATEMENT REGARDING SEQUENCE LISTING

Applicant submits herewith a Sequence Listing in computer readable form and in compliance with 37 C.F.R. §§ 1.821-1.825. This sequence listing is in ASCII TXT format with filename "11001-034US2_2021_10_28_ Sequence Listing," a 609 byte file size, and creation date of Nov. 11, 2017. The content of the Sequence Listing is hereby incorporated by reference.

FIELD

The present disclosure relates to methods for detecting and treating propranolol sensitive tumors.

BACKGROUND

Infantile hemangiomas (IH) are highly vascularized benign tumors diagnosed in 3-10% of children before they are one year old. IH lesions have a unique pattern of growth in which the initial phase of rapid proliferation is followed by slow spontaneous involution that leaves behind a fibro-fatty residuum. During the proliferative phase, immature endothelial cells, positive for glucose transporter-1 (GLUT1), form aberrant blood vessels, rich in α-smooth muscle actin-positive pericytes and mast cells. This endothelial GLUT1 expression distinguishes IH from other types of vascular tumors and vascular malformations. Stem cell reprograming factors OCT4, SOX2, NANOG and MYC are also highly expressed in IH.

Serendipitously, it was discovered by Léauté-Labrèze that the non-selective beta-adrenergic receptor blocker, propranolol, triggers early involution of IH. Consequently, propranolol has become the first line therapy for IH. IH represents a unique model to study postnatal vasculogenesis and vessel regression. Despite the prevalence of these tumors, the complex pathogenesis of IH is poorly understood. Thus, what is needed are novel biomarkers for use in methods of detecting and treating propranolol sensitive tumors and cancers.

The methods disclosed herein address these and other needs.

SUMMARY

Disclosed herein are novel methods for detecting and treating propranolol sensitive cancers. Herein, the inventor has uncovered the role of the LIN28B/let-7 switch in infantile hemangioma (IH) pathogenesis and provides a novel mechanism by which propranolol induces IH involution. In addition, this is the first known report to show that propranolol reduces the proliferation of iPSCs and induces epithelial-mesenchymal transition (EMT) and adipogenesis. Thus, this report provides novel therapeutic methods for detecting and treating tumors and cancers with propranolol in which the LIN28/let-7 pathway is imbalanced.

In some aspects, disclosed herein is a method of treating a subject having a tumor, comprising:
  obtaining a biological sample derived from the subject having a tumor;
  quantifying an expression level of one or more biomarkers that are associated with responsiveness of the tumor to propranolol treatment in the biological sample derived from the subject relative to a reference control, wherein the biomarker comprises one or more of LIN28B, LIN28A, or let-7;
  determining the tumor as responsive to propranolol treatment if the expression level of one or more of the biomarkers LIN28B or LIN28A is higher in the biological sample derived from the subject compared to the reference control, or
  determining the tumor as responsive to propranolol treatment if the expression level of let-7 is lower in the biological sample derived from the subject compared to the reference control; and
  administering to the subject a therapeutically effective amount of propranolol.

In some embodiments, the biomarker comprises LIN28B. In some embodiments, the biomarker comprises LIN28A. In some embodiments, the biomarker comprises let-7.

In some embodiments, the biological sample comprises one or a combination of biopsy tissue, tumor cells, or a blood sample. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the tumor is a cancer. In some embodiments, the cancer is selected from a brain cancer, breast cancer, or cervical cancer. In some embodiments, the subject is a human.

In some aspects, disclosed herein is a method for predicting the responsiveness of a tumor to propranolol treatment, comprising:
  obtaining a biological sample derived from a subject having a tumor;
  quantifying an expression level of one or more biomarkers that are associated with responsiveness of the tumor to propranolol treatment in the biological sample derived from the subject relative to a reference control, wherein the biomarker comprises one or more of LIN28B, LIN28A, or let-7; and
  predicting one of:
    the tumor as responsive to propranolol treatment if the expression level of one or more of the biomarkers LIN28B or LIN28A is higher in the biological sample derived from the subject compared to the reference control, or
    the tumor as responsive to propranolol treatment if the expression level of let-7 is lower in the biological sample derived from the subject compared to the reference control.

In some embodiments, the biomarker comprises LIN28B. In some embodiments, the biomarker comprises LIN28A. In some embodiments, the biomarker comprises let-7.

In some embodiments, the biological sample comprises one or a combination of biopsy tissue, tumor cells, or a blood sample. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the method further comprises administering propranolol to the subject based on the prediction of the subject as having a propranolol responsive tumor.

In some embodiments, the tumor is a cancer. In some embodiments, the cancer is selected from a brain cancer, breast cancer, or cervical cancer. In some embodiments, the subject is a human.

BRIEF DESCRIPTION OF THE DRAWINGS

The accompanying figures, which are incorporated in and constitute a part of this specification, illustrate several aspects described below.

DETAILED DESCRIPTION

Figure 1:
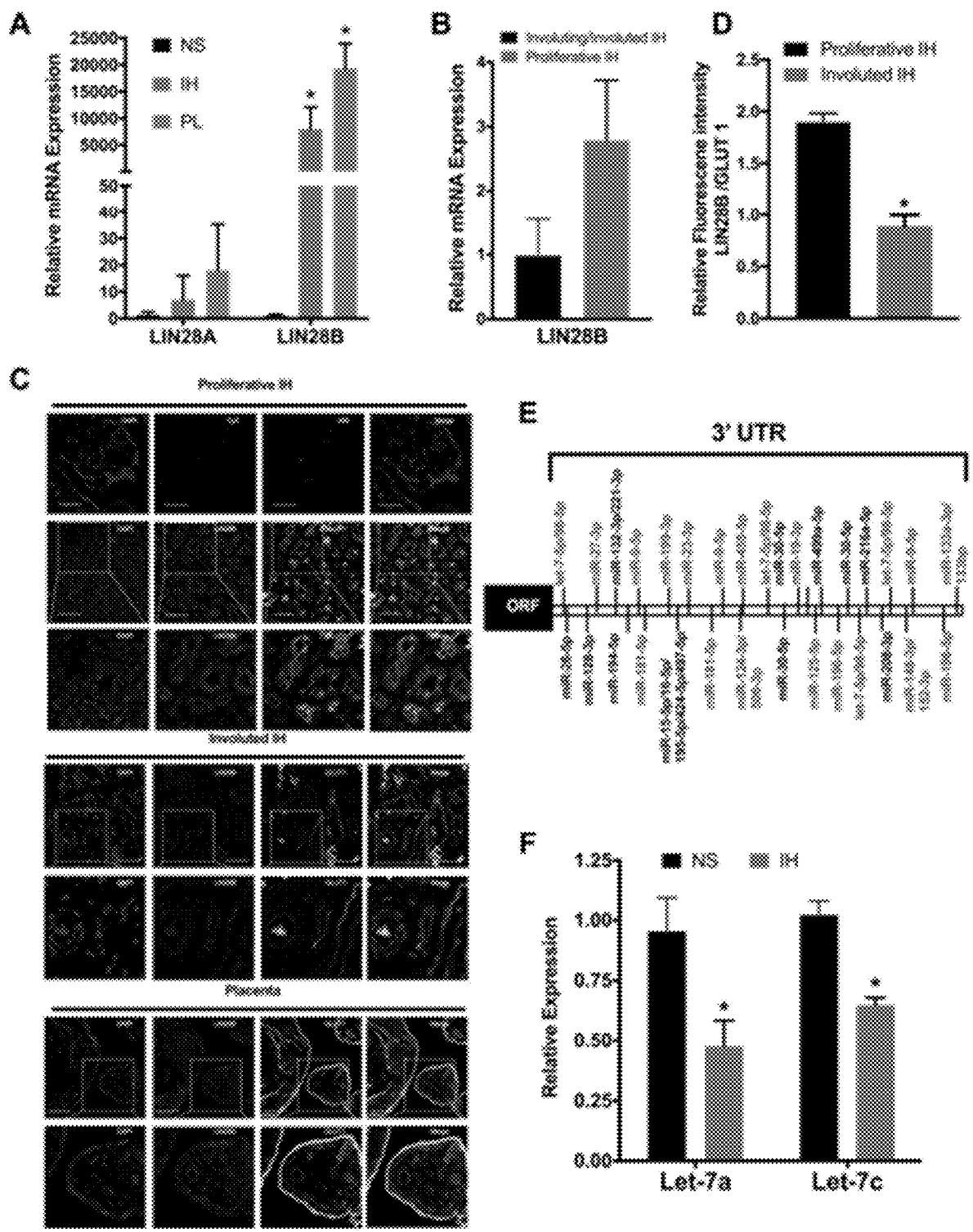
FIG. 1. LIN28B is highly expressed in proliferative infantile hemangioma (IH). (A and B) qRT-PCR analysis of LIN28A and LIN28B (A) or LIN28B (B) expression normalized to GAPDH. IH (n=4), NS (n=4), normal term placenta (PL, n=4), proliferative IH (n=2) and involuting/involuted IH (n=2). (C) Representative immunostaining for LIN28B and GLUT1 of proliferative IH (n=4), involuting/involuted IH (n=5) and term placenta (n=3) samples. Nuclei were counterstained with DAPI. No positive immunostaining was observed in the negative control sections (Alexa Fluor 488 or cy3). Scale bars: 50 µm; original magnification, ×60 and ×120 (insets). (D) Quantification of LIN28B/GLUT1 fluorescence signal ratio in proliferative and involuted IF samples. (E) Predicted miRNAs target sites in LIN28B 3'UTR (TargetScan Human Release 7.1). In red, downregulated miRNA in sRNAseq analysis of IH vs. NS. (F) qRT-PCR analysis of let-7a and let-7c expression in IH (n=4) and NS (n=4). Graphs represent means±SEM. * $p<0.05$ vs. NS (A and F), vs proliferative IH (D) by one-way ANOVA with Dunnett's post hoc test (A) or two-tailed Student's t-test (D and F).

Disclosed herein are novel methods for detecting and treating propranolol sensitive cancers. Herein, the inventor has uncovered the role of the LIN28B/let-7 switch in infantile hemangioma (IH) pathogenesis and provides a novel mechanism by which propranolol induces IH involution. In addition, this is the first known report to show that propranolol reduces the proliferation of iPSCs and induces epithelial-mesenchymal transition (EMT) and adipogenesis. Thus, this report provides novel therapeutic methods for detecting and treating tumors and cancers with propranolol in which the LIN28/let-7 pathway is imbalanced.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

As used herein, the terms "may," "optionally." and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

The term "subject" or "host" refers to any individual who is the target of administration or treatment. The subject can be a vertebrate, for example, a mammal. Thus, the subject can be a human or veterinary patient. The term "patient" refers to a subject under the treatment of a clinician, e.g., physician. The subject can be either male or female.

The terms "peptide," "protein," and "polypeptide" are used interchangeably to refer to a natural or synthetic molecule comprising two or more amino acids linked by the carboxyl group of one amino acid to the alpha amino group of another.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T/U, or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, at least about 75%, or at least about 90% complementary. See Kanehisa (1984) Nucl. Acids Res. 12:203.

"Hybridization" refers to the process in which two single-stranded oligonucleotides bind non-covalently to form a stable double-stranded oligonucleotide. The term "hybridization" may also refer to triple-stranded hybridization. The resulting (usually) double-stranded oligonucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. In certain exemplary embodiments, hybridization takes place at room temperature. The term "stringent hybridization conditions" as used herein is the binding which occurs within a range from about Tm 5° C. (5° C. below the melting temperature Tm of the probe) to about 20° C. to 25° C. below Tm. The term "highly stringent hybridization conditions" as used herein refers to conditions of: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

Methods of Diagnosis and Treatment

In some aspects, disclosed herein is a method of treating a subject having a tumor, comprising:
  obtaining a biological sample derived from the subject having a tumor;
  quantifying an expression level of one or more biomarkers that are associated with responsiveness of the tumor to propranolol treatment in the biological sample derived from the subject relative to a reference control, wherein the biomarker comprises one or more of LIN28B, LIN28A, or let-7;
  determining the tumor as responsive to propranolol treatment if the expression level of one or more of the biomarkers LIN28B or LIN28A is higher in the biological sample derived from the subject compared to the reference control, or
  determining the tumor as responsive to propranolol treatment if the expression level of let-7 is lower in the biological sample derived from the subject compared to the reference control; and
  administering to the subject a therapeutically effective amount of propranolol.

In some embodiments, the biomarker comprises LIN28B. In some embodiments, the biomarker comprises LIN28A. In some embodiments, the biomarker comprises let-7.

In some embodiments, the biological sample comprises one or a combination of biopsy tissue, tumor cells, blood sample, serum sample, or tumor tissue. In some embodiments, the biological sample comprises a blood sample. In some embodiments, the biological sample comprises a serum sample. In some embodiments, the biological sample comprises biopsy tissue. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the quantifying is carried out to detect protein expression levels. In some embodiments, the quantifying is carried out by one or a combination of Western blot, ELISA, flow cytometry, immunohistochemistry, and other methods of detection using antibodies. In some embodiments, the quantifying is carried out to detect gene methylation and gene copy number.

In some embodiments, the method further comprises administering propranolol to the subject based on the prediction of the subject as having a propranolol responsive tumor.

In some embodiments, the tumor is a cancer. In some embodiments, the cancer is selected from a brain cancer, breast cancer, or cervical cancer. In some embodiments, the subject is a human.

In some aspects, disclosed herein is a method for predicting or determining the responsiveness of a tumor to propranolol treatment, comprising:
  obtaining a biological sample derived from a subject having a tumor;
  quantifying an expression level of one or more biomarkers that are associated with responsiveness of the tumor to propranolol treatment in the biological sample derived from the subject relative to a reference control, wherein the biomarker comprises one or more of LIN28B, LIN28A, or let-7; and
  predicting or determining one of:
    the tumor as responsive to propranolol treatment if the expression level of one or more of the biomarkers LIN28B or LIN28A is higher in the biological sample derived from the subject compared to the reference control, or
    the tumor as responsive to propranolol treatment if the expression level of let-7 is lower in the biological sample derived from the subject compared to the reference control.

In some embodiments, the biomarker comprises LIN28B. In some embodiments, the biomarker comprises LIN28A. In some embodiments, the biomarker comprises let-7.

In some embodiments, the biological sample comprises one or a combination of biopsy tissue, tumor cells, blood sample, serum sample, or tumor tissue. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the tumor is a hemangioma. In some embodiments, the tumor is an infantile hemangioma.

In some embodiments, the tumor is a cancer. In some embodiments, the cancer is selected from a brain cancer, breast cancer, cervical cancer, prostate cancer, gastrointestinal cancer, renal cell carcinoma, pediatric cancer, hepatocellular carcinoma, neuroblastoma, melanoma, endometrial carcinosarcoma, epithelial ovarian cancer, peripheral T-cell lymphoma, primitive neurol-ectodermal tumor, epithelial tumor, Esophagus cancer, lung cancer, non-small cell lung cancer, ovarian adenocarcinoma, ovarian primitive germ cell tumor, colon cancer, renal cell cancer, nasopharyngeal carcinoma, medulloblastoma, serous ovarian cancer, rhabdoid tumor, testicular germ cell tumors, extragonadal germ cell tumor, or epithelial ovarian cancer. In some embodiments, the cancer is a brain cancer. In some embodiments, the brain cancer is glioma (low grade glioma or high grade glioma). In some embodiments, the brain cancer is glioblastoma. In some embodiments, the brain cancer is a pediatric brain cancer. In some embodiments, the brain cancer is embryonal tumor with multilayered rosettes (ETMR).

In some embodiments, the subject is a human.

In some embodiments, the tumor expresses high levels of LIN28B. In some embodiments, the tumor expresses high levels of LIN28A. In some embodiments, the tumor expresses high levels of mir-498(46). In some embodiments, the tumor expresses low levels of let-7. In some embodiments, the cancer expresses high levels of LIN28B. In some embodiments, the cancer expresses high levels of LIN28A. In some embodiments, the cancer expresses high levels of mir-498(46). In some embodiments, the cancer expresses low levels of let-7.

In some embodiments, the reference control is the expression level of the biomarker from a subject without a tumor or a cancer (a non-diseased subject). In some embodiments, the reference control is the expression level of the biomarker from a healthy tissue from the subject (a non-cancerous cell from the subject). In some embodiments, the reference control is a healthy control. In some embodiments, the reference control is a non-cancerous control. In some embodiments, the reference control is from a pooled population of patient samples or biological samples.

In some embodiments, the expression of the biomarker is at least about 10% higher (for example, about 10% higher, about 20% higher, about 30% higher, about 40% higher, about 50% higher, about 60% higher, about 70% higher, about 80% higher, about 90% higher, about 100% higher, and more) in the biological sample than the reference control. In some embodiments, the expression of the biomarker is at least about 10% lower (for example, about 10% higher, about 20% higher, about 30% higher, about 40% higher, about 50% higher, about 60% higher, about 70% higher, about 80% higher, about 90% higher, about 100% higher, and more) in the biological sample than the reference control.

In some embodiments, the method further comprises administering propranolol to the subject based on the prediction of the subject as having a propranolol responsive tumor.

Propranolol is a nonselective beta1 and beta2 adrenergic receptor blocker and is typically used to treat patients with heart diseases and hypertension. Propranolol is also used to treat hemangiomas, although the mechanism of how propranolol reduces hemangiomas is unclear. In addition to propranolol, other beta blockers can also be administered in the methods herein.

In some aspects, disclosed herein is a method of treating a subject having a tumor, comprising:
obtaining a biological sample derived from the subject having a tumor;
quantifying an expression level of one or more biomarkers that are associated with responsiveness of the tumor to a beta-blocker treatment in the biological sample derived from the subject relative to a reference control, wherein the biomarker comprises one or more of LIN28B, LIN28A, or let-7;
determining the tumor as responsive to the beta-blocker treatment if the expression level of one or more of the biomarkers LIN28B or LIN28A is higher in the biological sample derived from the subject compared to the reference control, or
determining the tumor as responsive to the beta-blocker treatment if the expression level of let-7 is lower in the biological sample derived from the subject compared to the reference control; and
administering to the subject a therapeutically effective amount of the beta-blocker.

In some aspects, disclosed herein is a method for predicting the responsiveness of a tumor to a beta-blocker treatment, comprising:
obtaining a biological sample derived from a subject having a tumor;
quantifying an expression level of one or more biomarkers that are associated with responsiveness of the tumor to the beta-blocker treatment in the biological sample derived from the subject relative to a reference control, wherein the biomarker comprises one or more of LIN28B, LIN28A, or let-7; and
predicting one of:
the tumor as responsive to the beta-blocker treatment if the expression level of one or more of the biomarkers LIN28B or LIN28A is higher in the biological sample derived from the subject compared to the reference control, or
the tumor as responsive to the beta-blocker treatment if the expression level of let-7 is lower in the biological sample derived from the subject compared to the reference control.

In one embodiment, the beta-blocker is selected from propranolol, timolol, betaxolol, nadolol, alprenolol, acebutolol, atenolol, bisoprolol, carvedilol, carteolol, levobunolol, mepindolol, metipranolol, labetalol, metoprolol, nebivolol, oxprenolol, penbutolol, pindolol, sotalol, a pharmaceutically acceptable salt thereof, or a combination thereof. In one embodiment, the beta-blocker comprises propranolol.

In some embodiments herein, the biomarker comprises one or more of LIN28B, LIN28A, or let-7; and further comprises mir-498(46).

In some aspects, disclosed herein is a method of treating a subject having a tumor, comprising:
obtaining a biological sample derived from the subject having a tumor;
quantifying an expression level of one or more biomarkers that are associated with responsiveness of the tumor to propranolol treatment in the biological sample derived from the subject relative to a reference control, wherein the biomarker comprises one or more of LIN28B, LIN28A, mir-498(46), let-7, or a combination thereof;
determining the tumor as responsive to propranolol treatment if the expression level of one or more of the biomarkers LIN28B, LIN28A, or mir-498(46), is higher in the biological sample derived from the subject compared to the reference control, and/or
determining the tumor as responsive to propranolol treatment if the expression level of let-7 is lower in the biological sample derived from the subject compared to the reference control; and
administering to the subject a therapeutically effective amount of propranolol.

In some aspects, disclosed herein is a method for predicting the responsiveness of a tumor to propranolol treatment, comprising:
obtaining a biological sample derived from a subject having a tumor;
quantifying an expression level of one or more biomarkers that are associated with responsiveness of the tumor to propranolol treatment in the biological sample derived from the subject relative to a reference control, wherein the biomarker comprises one or more of LIN28B, LIN28A, mir-498(46), let-7, or a combination thereof; and predicting:
the tumor as responsive to propranolol treatment if the expression level of one or more of the biomarkers LIN28B, LIN28A, or mir-498(46) is higher in the biological sample derived from the subject compared to the reference control, and/or the tumor as responsive to propranolol treatment if the expression level of let-7 is lower in the biological sample derived from the subject compared to the reference control.

In some aspects, disclosed herein is a method for the preventative or curative treatment of
a cancer in a subject, comprising:
obtaining a biological sample derived from the subject;
quantifying an expression level of one or more biomarkers that are associated with responsiveness of the tumor to a beta-blocker treatment in the biological sample derived from the subject relative to a reference control, wherein the biomarker comprises one or more of LIN28B or LIN28A;
determining the tumor as responsive to the beta-blocker treatment if the expression level of one or more of the biomarkers LIN28B or LIN28A is higher in the biological sample derived from the subject compared to the reference control; and then
administering to the subject a therapeutically effective amount of the beta-blocker.

In some aspects, disclosed herein is a method for the preventative or curative treatment of a cancer in a subject, comprising:
obtaining a biological sample derived from the subject;
quantifying an expression level of one or more biomarkers that are associated with responsiveness of the tumor to a beta-blocker treatment in the biological sample derived from the subject relative to a reference control, wherein the biomarker comprises let-7;
determining the tumor as responsive to the beta-blocker treatment if the expression level of let-7 is lower in the biological sample derived from the subject compared to the reference control; and then
administering to the subject a therapeutically effective amount of the beta-blocker.

In some aspects, disclosed herein is a method for the preventative or curative treatment of a cancer in a subject, comprising:
obtaining a biological sample derived from the subject;
quantifying an expression level of one or more biomarkers that are associated with responsiveness of the tumor to propranolol treatment in the biological sample derived from the subject relative to a reference control, wherein the biomarker comprises one or more of LIN28B or LIN28A;
determining the tumor as responsive to propranolol treatment if the expression level of one or more of the biomarkers LIN28B or LIN28A is higher in the biological sample derived from the subject compared to the reference control; and then
administering to the subject a therapeutically effective amount of propranolol.

In some aspects, disclosed herein is a method for the preventative or curative treatment of a cancer in a subject, comprising:
obtaining a biological sample derived from the subject;
quantifying an expression level of one or more biomarkers that are associated with responsiveness of the tumor to propranolol treatment in the biological sample derived from the subject relative to a reference control, wherein the biomarker comprises let-7;
determining the tumor as responsive to propranolol treatment if the expression level of let-7 is lower in the biological sample derived from the subject compared to the reference control; and then
administering to the subject a therapeutically effective amount of propranolol.

In one embodiment of the present disclosure, a kit is provided for determining or predicting the responsiveness of a tumor to propranolol treatment, the kit comprising:
primers for quantifying a gene expression level of one or more biomarkers that are associated with responsiveness of the tumor to propranolol treatment in a biological sample derived from a subject relative to a reference control, wherein the primers are for one or more biomarkers comprising LIN28B, LIN28A, let-7, or a combination thereof; and
instructions for determining or predicting one of:
the tumor as responsive to propranolol treatment if the expression level of one or more of the biomarkers LIN28B or LIN28A is higher in the biological sample derived from the subject compared to the reference control, or
the tumor as responsive to propranolol treatment if the expression level of let-7 is lower in the biological sample derived from the subject compared to the reference control.

In some embodiments, in addition to a beta blocker (for example, propranolol), an additional chemotherapeutic agent can also be administered in combination with the beta-blocker (for example, propranolol) to a subject. Additional chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antis, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B. Cytoxan, Dacarbazine, Dactinomycin, dactinomycin (formerly actinomycin), daunirubicin HCL, daunorubicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional chemotherapeutic agents or therapeutic agents that can be administered in combination with the compounds disclosed herein can also include bevacizumab, sutinib, sorafenib, 2-methoxyestradiol, finasunate, vatalanib, vandetanib, aflibercept, volociximab, etaracizumab, cilengitide, erlotinib, cetuximab, panitumumab, gefitinib, trastuzumab, atacicept, rituximab, alemtuzumab, aldesleukine, atlizumab, tocilizumab, temsirolimus, everolimus, lucatumumab, dacetuzumab, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, oblimersen, plitidepsin, talmapimod, enzastaurin, tipifarnib, perifosine, imatinib, dasatinib, lenalidomide, thalidomide, simvastatin, and celecoxib.

Nomenclature abbreviations for genes and proteins can be found in the HUGO database (genenames.org), where the sequences for the DNA, RNA, and proteins can be found: LIN28B, HGNC:32207; LIN28A, HGNC: 15986. Nomenclature abbreviations for miRNA (miR) sequences can be found in the miRBase database (mirbase.org). "Let-7" as used herein refers to the let-7 family of miRs, where the miR sequences are known by one of skill in the art to be located in the miRBase database (version 22, released on March 2018, mirbase.org): hsa-let-7a-1 (MI0000060), hsa-let-7a-2 (MI0000061), hsa-let-7a-3 (MI0000062), hsa-let-7b (MI0000063), hsa-let-7c (MI0000064), hsa-let-7d (MI0000065), hsa-let-7e (MI0000066), hsa-let-7f-1 (MI0000067), hsa-let-7f-2 (MI0000068), hsa-let-7g (MI0000433), hsa-let-7i (MI0000434), hsa-mir-98 (MI0000100). "mir-498(46)" as used herein refers to the mir-498(46) family of miRs, where the miR sequences are known by one of skill in the art to be located in the miRBase database (version 22, released on March 2018, mirbase.org): hsa-mir-520c (MI0003143), hsa-mir-515-1 (MI0003144), hsa-mir-519c (MI0003145), hsa-mir-520f (MI0003146), hsa-mir-515-2 (MI0003147), hsa-mir-519c (MI0003148), hsa-mir-520a (MI0003149), hsa-mir-526b (MI0003150), hsa-mir-519b (MI0003151), hsa-mir-525 (MI0003152), hsa-mir-523 (MI0003153), hsa-mir-518f (MI0003154), hsa-mir-520b (MI0003155), hsa-mir-518b (MI0003156), hsa-mir-526a-1 (MI0003157), hsa-mir-520c (MI0003158), hsa-mir-518c (MI0003159), hsa-mir-524 (MI0003160), hsa-mir-517a (MI0003161), hsa-mir-519d (MI0003162), hsa-mir-521-2 (MI0003163), hsa-mir-520d (MI0003164), hsa-mir-517b (MI0003165), hsa-mir-520g (MI0003166), hsa-mir-516b-2 (MI0003167), hsa-mir-526a-2 (MI0003168), hsa-mir-518c (MI0003169), hsa-mir-518a-1 (MI0003170), hsa-mir-518d (MI0003171), hsa-mir-516b-1 (MI0003172), hsa-mir-518a-2 (MI0003173), hsa-mir-517c (MI0003174), hsa-mir-520h (MI0003175), hsa-mir-521-1 (MI0003176), hsa-mir-522 (MI0003177), hsa-mir-519a-1 (MI0003178), hsa-mir-527 (MI0003179), hsa-mir-516a-1 (MI0003180), hsa-mir-516a-2 (MI0003181), hsa-mir-519a-2 (MI0003182), hsa-mir-1283-1 (MI0003832), hsa-mir-1283-2 (MI0006430).

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Modulation of LIN28B/Let-7 Signaling by Propranolol Contributes to Infantile Hemangioma Involution Infantile hemangiomas (IH) are the most common benign vascular neoplasms of infancy, characterized by a rapid growth phase followed by a spontaneous involution, or triggered by propranolol treatment by poorly understood mechanisms. LIN28/let-7 axis plays a central role in the regulation of stem cell self-renewal and tumorigenesis. However, the role of LIN28B/let-7 signaling in IH pathogenesis has not yet been elucidated.

LIN28B is highly expressed in proliferative IH and is less expressed in involuted and in propranolol treated IH samples as measured by immunofluorescence staining and qRT-PCR. Small RNA sequencing analysis of IH samples revealed a decrease in microRNAs that target LIN28B, including let-7, and an increase in microRNAs in the mir-498(46) cluster. Overexpression of LIN28B in HEK293 cells induced the expression of miR-516b in the mir-498(46) cluster. Propranolol treatment of induced pluripotent stem cells (iPSCs), which express mir-498(46) endogenously, reduced the expression of both LIN28B and mir-498(46) and increased the expression of let-7. Furthermore, propranolol treatment reduced the proliferation of iPSCs and induced epithelial-to-mesenchymal transition.

This work uncovers the role of the LIN28B/let-7 switch in IH pathogenesis and provides a novel mechanism by which propranolol induces IH involution. Furthermore, it provides therapeutic implications for cancers in which the LIN28/let-7 pathway is imbalanced.

Background

Infantile hemangiomas (IH) are highly vascularized benign tumors diagnosed in 3-10% of children before they are one year old[1]. IH lesions have a unique pattern of growth in which the initial phase of rapid proliferation is followed by slow spontaneous involution that leaves behind a fibrofatty residuum[2]. During the proliferative phase, immature endothelial cells, positive for glucose transporter-1 (GLUT1), form aberrant blood vessels, rich in α-smooth muscle actin-positive pericytes and mast cells[3]. This endothelial GLUT1 expression distinguishes IH from other types of vascular tumors and vascular malformations[4, 5]. Stem cell reprograming factors OCT4, SOX2, NANOG and MYC are also highly expressed in IH[6].

The chromosome 19 microRNA (miRNA) cluster (C19MC), referred to as miRNA cistron mir-498(46) or mir-498(46), was recently reported to be highly expressed in IH[7]. Mir-498(46) is unique to primates and is the largest known human miRNA gene cluster that spans over 100 kb and contains 46 miRNA genes flanked by Alu elements[8].

Expression of miRNA genes in this cluster is restricted to the placenta, embryonic stem cell (ESC) and certain tumors[8-11].

While some studies have shown considerable similarity between IH and placental transcriptomes[12], which suggests a placental origin for proliferating cells in IH[13], other studies propose that IH originate from hemangioma stem cells[14]. In support of the latter notion, human CD133+ hemangioma stem cells (HemSCs) implanted subcutaneously into immunodeficient mice induce GLUT1-positive microvessels, which are gradually replaced by adipocytes, thereby reproducing the IH involution phase. Importantly, when grown in culture, GLUT1-positive/mir-498(46)-expressing endothelial cells, isolated from proliferative IH, lose the expression of mir-498(46) and GLUT1 and undergo an endothelial-mesenchymal transition (EndMT), a process similar to epithelial-mesenchymal transition (EMT)[7, 15].

Serendipitously, it was discovered by Léauté-Labrèze that the non-selective beta-adrenergic receptor blocker, propranolol, triggers early involution of IH[16]. Consequently, propranolol has become the first line therapy for IH[17]. Previous work has shown that propranolol-treated IH tumors contain significantly lower levels of mir-498(46) than proliferative IH[7]. Moreover, levels of circulating mir-498(46) fall during the involution phase and correlate with the clinical response to propranolol treatment[7], suggesting the potential involvement of mir-498(46) in the pathogenesis of IH.

The self-renewal capacity of ESCs is regulated in part by a set of interactive gene products, LIN28 and the let-7 family of miRNAs. Two human LIN28 paralogs, LIN28A and LIN28B, are highly expressed in ESCs. They inhibit the post-transcriptional maturation of let-7 miRNAs and influence mRNA translation[18, 19]. Conversely, let-7 negatively regulates the expression of LIN28 by interacting with the 3' untranslated regions of both LIN28A and LIN28B mRNAs[20]. This interaction creates a double negative feedback loop, which is highly conserved. Ectopic expression of LIN28A or LIN28B alongside the reprogramming factors Oct4, Sox2, and Nanog[21-23] has been successfully used to generate induced pluripotent stem cells (iPSCs) from fibroblasts. In addition, LIN28B overexpression has been successfully used to generate iPSCs from fibroblasts[24].

EMT is the biological process through which normally polarized epithelial cells lose their apical-basal polarity and acquire a mesenchymal cell phenotype characterized by enhanced migration and invasiveness, resistance to apoptosis and increased deposition of extracellular matrix components[24]. This trans-differentiation is mediated by key transcription factors such as SNAIL, SLUG, TWIST1 and ZEB that regulate downstream epithelial markers, which among other effects, leads to decreased E-cadherin levels and increased expression of mesenchymal cell markers, such as N-cadherin and vimentin[25]. iPSC generation from fibroblasts requires suppression of EMT and activation of mesenchymal-epithelial transition (MET) signals[26].

IH represents a unique model to study postnatal vasculogenesis and vessel regression. Despite the prevalence of these tumors, the complex pathogenesis of IH is poorly understood. In this example, LIN28B was found to be highly expressed in proliferative IH samples and is downregulated both in involuted and propranolol-treated IH samples. Consistent with those observations, in vitro treatment of iPSCs with propranolol caused a decrease in LIN28B, mir-498(46) expression, decreased cell proliferation and increased the expression of let-7 family of miRNAs and EMT genes. These results show the role of LIN28 and let-7 in the pathogenesis of IH and offers a new mechanism by which propranolol induces involution of IH, and provides for new methods of treating propranolol sensitive tumors.

Results

LIN28B is Highly Expressed in Proliferative IH and is Reduced Upon Involution

IH are derived from dysregulated stem cells[41] and represent a unique tumor model characterized by a proliferative phase followed by spontaneous involution, regulated by yet unknown mechanisms. Given the key role of the LIN28/let-7 axis in governing stem cell self-renewal and cell differentiation, the expression levels of LIN28A and LIN28B were first assessed in IH samples by qRT-PCR and compared to normal infant skin (NS) and samples of normal human placentas at term. IH samples exhibited a 7- and 7500-fold increase ($p<0.05$) in LIN28A and LIN28B, respectively, compared to NS (FIG. 1A). The expression levels of LIN28A and LIN28B in IH were comparable to their expression levels in the placenta (FIG. 1A).

Given the dramatic increase of LIN28B expression in IH, all subsequent experiments were focused on LIN28B. To determine if LIN28B is differentially expressed in proliferative IH compared to involuting/involuted IH, LIN28B expression was assessed by qRT-PCR and found that it was 2.7-fold higher ($p<0.33$) in proliferative compared to involuting/involuted IH samples (FIG. 1B).

To determine LIN28B cellular localization, dual immunofluorescence staining for LIN28B and the IH marker, GLUT1, was performed in paraffin embedded IH sections obtained from proliferative and involuted IH specimens. Term placenta samples were used as positive controls. In proliferative IH samples, LIN28B was highly expressed and co-localized with the GLUT1 positive endothelial cells as well as perivascular non-endothelial cells, whereas involuted IH samples showed weak staining for both LIN28B and GLUT1 (FIG. 1C). It was found in term placentas that LIN28B and GLUT1 were co-localized in trophoblast and endothelium of chorionic villi (FIG. 1C). Quantifications of LIN28B to GLUT1 immunofluorescence signal intensities showed ~2-fold increase in proliferative IH compared to involuted IH samples (FIG. 1D). These data confirm the increased expression of LIN28B in proliferative IH and its localization in GLUT1-positive endothelial cells and perivascular non-endothelial cells that may display properties of facultative stem cells[15].

The let-7 miRNA family and numerous other miRNAs negatively regulate LIN28B by binding to its 3'UTR (FIG. 1E). To determine whether the increase in LIN28B in IH samples is associated with decreased expression of these miRNAs, small RNA sequencing (sRNAseq) analysis was performed on eight IH and five NS samples. Looking at the most abundant, or highly expressed, miRNAs (i.e. consuming the top 90% of sequencing reads) in IH compared to NS samples showed 32 significantly changed miRNA cistrons (FDR 0.25), of which 21 were upregulated in IH and 11 downregulated in IH compared to NS (Table 1). Of the 21 upregulated miRNA cistrons, mir-498(46) was most extensively upregulated with a 492-fold increase (Table 1). The downregulated cistrons include miRNAs that are predicted to bind to LIN28B 3'UTR, namely let-7a, let-7c, let-7f, let-7g. let-7i, miR-19b(2), miR-506(1), miR-196a/b, miR-455-5p(1), miR-9(3), miR-124(3), miR-27a(1), miR-27b(1), miR-23b(1), miR-125b(2), miR-199b-5p(1), miR-19a(1) and miR-148a(1), which were 2- to 45.6-fold downregulated. Importantly, let-7, miR-196 and miR-9 bind to multiple target sites on LIN28B 3' UTR (FIG. 1E). These data indicate that the upregulation of LIN28B in IH may be due, at least in part, to its decreased post-transcriptional regulation by miRNAs. Additionally, LIN28B is an established repressor of miRNA biogenesis[42], among which let-7 is the most extensively studied[43]. Consequently, sRNAseq analysis of IH and NS revealed that let-7g(1), let-7c(1), and miR-200c(1) were 2.9-, 3.6- and 135-fold downregulated, respectively, in IH compared to NS. To determine whether additional members of the let-7 family were affected, yet did not pass the sRNAseq analysis filters, qRT-PCR analysis was performed for randomly selected members let-7a and let-7c. It was found that both were downregulated (p<0.05) in IH compared to NS (FIG. 1F).

LIN28B Activates Mir-498(46) miRNAs Independently of the Upstream CpG-Island

Figure 2:
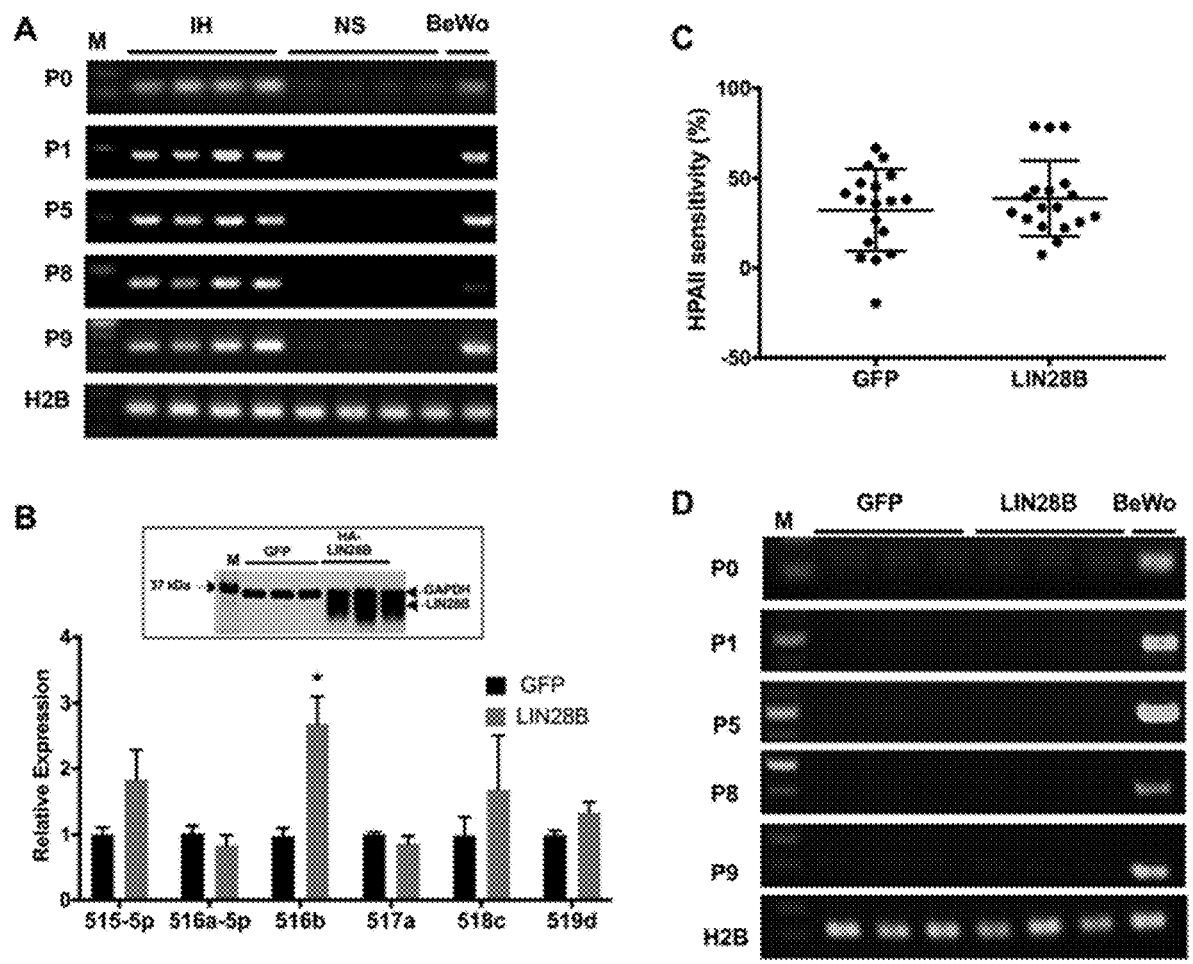
FIG. 2. LIN28B increases the expression of miRNAs of the mir-498(46) cistron. (A) RT-PCR analysis using P0, P1, P5, P8 and P9 primer sets reveal the presence of transcripts generated upstream of mir-498(46) in IH (n=4) but not in NS. BeWo cells were used as positive control and H2B as reference gene. (B-D) HEK293 cells were transfected with FLAG-LIN28B or GFP control vector for 72 hours followed by (B) qRT-PCR analysis of six randomly selected miRNAs of the mir-498(46) cistron normalized to U18. Insert, representative immunoblot of LIN28B and GAPDH; (C) HPAII sensitivity assay of the mir-498(46) cistron CpG-island promoter region and (D) RT-PCR analysis as described in A. Data represents means±SEM of 3 independent experiments. * $p<0.05$ vs. GFP transfected cells by Mann-Whitney U test.

The expression of mir-498(46) is controlled by methylation of an upstream CpG-rich promoter region that includes a transcription start site located ~17 kb upstream of the first miRNA gene[30]. To test whether the increase in mir-498(46) expression found in IH samples is due to transcriptional activation of the upstream CpG-rich island, qRT-PCR was performed using primer sets designed to amplify regions downstream of the CpG-island, as previously described[30]. The trophoblast-derived choriocarcinoma BeWo cell line, which endogenously expresses mir-498(46), was used as a positive control. IH samples and BeWo cells displayed active transcription starting at the ~17 kb upstream mir-498 (46) CpG-related promoter region, whereas no transcripts were found in NS samples (FIG. 2A). This indicates that the promoter region upstream of mir-498(46) is transcriptionally active in IH.

Given that LIN28B expression is 7000-fold higher in IH than NS, a possible positive regulation of mir-498(46) miRNAs by LIN28B was tested. To that end, HEK293 cells were transiently transfected with a LIN28B-coding plasmid, and the expression levels of LIN28B and of six randomly selected miRNAs of mir-498(46) miRNAs were measured after 72 h by immunoblotting and qRT-PCR, respectively. Interestingly, overexpression of LIN28B enhanced the expression of miR-516b by more than 2.6-fold (p<0.05), but did not significantly alter the expression of miR-515-5p, miR-516a-5p, miR-517a, miR-518c and miR-519d (FIG. 2B).

To test whether LIN28B affects the methylation of the ~17 kb CpG-island upstream of mir-498(46) which activates its transcription, an HpaII-sensitivity assay was performed followed by qPCR. Overexpression of LIN28B did not induce a significant increase in HpaII sensitivity of the CpG island (FIG. 2C) or induce transcriptional activation downstream of the CpG island (FIG. 2D). These data indicate that LIN28B induces the expression of mir-498(46) independently of the ~17 kb upstream promoter region.

Propranolol Inhibits LIN28B in IH and iPSC

Figure 3:
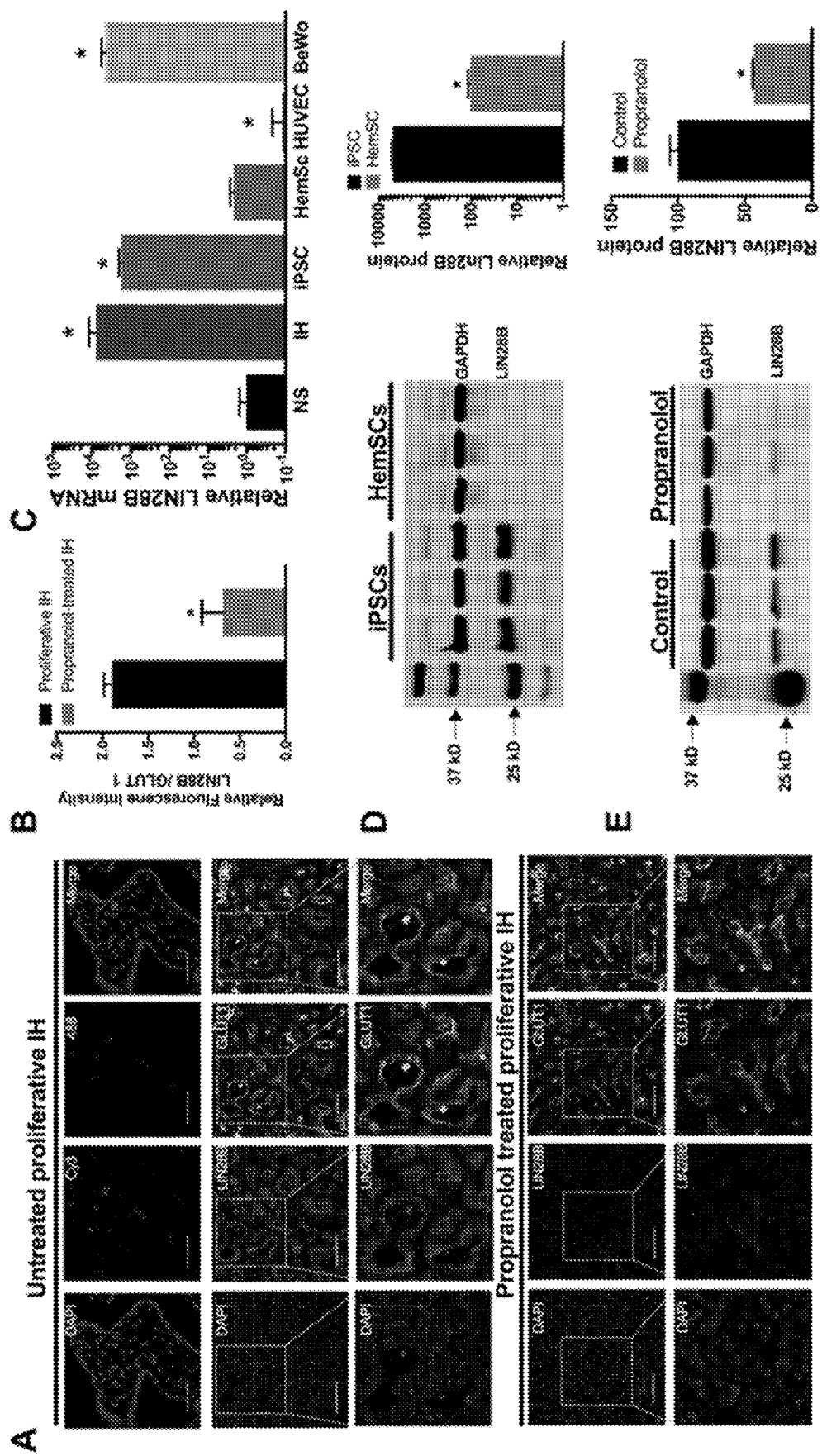
FIG. 3. Propranolol decreases the expression of LIN28B in IH treated patients and induced pluripotent stem cells (iPSCs). (A) Representative immunostaining for LIN28B and GLUT1 of proliferative IH (n=4) and propranolol treated proliferating IH (n=4) samples. Nuclei were counterstained with DAPI. No positive staining was observed in the negative control sections (Alexa Fluor 488 or Cy3). Scale bars: 50 µm; original magnification, ×60 and ×120 (insets).(B) Quantification of LIN28B/GLUT1 fluorescence signal ratio in proliferative and propranolol-treated samples. (C) qRT-PCR analysis of LIN28B expression normalized to GAPDH in IH, iPSC, HemSC (line H42, from 3 independent passages), HUVEC and BeWo cells compared to NS. (D and E) Representative immunoblot for LIN28B and GAPDH expression in (D) iPSC and HemSC line H42, from 3 independent passages and (E) iPSCs treated with 50 uM propranolol or vehicle control for 72 hours accompanied by densitometric quantification of LIN28B normalized to GAPDH. Data represent the mean±SEM of at least 3 independent experiments. * $p<0.05$ vs. proliferative IH (B), vs. NS (C), vs. iPSCs (D), or vs. vehicle control (E) by Student's t-test (B, D and E) or by one-way ANOVA with Dunnett's post hoc test (C).

The standard of care propranolol treatment of patients with IH induces rapid IH involution. To determine whether propranolol affects the expression of LIN28B in IH, dual immunofluorescence staining of LIN28B and the IH marker, GLUT1, was performed in paraffin embedded IH sections obtained from propranolol-treated proliferative IH and compared them to untreated proliferative IH samples. Both LIN28B and GLUT1 were markedly decreased in propranolol-treated proliferative IH compared to untreated proliferative IH (FIG. 3A). In addition, quantification of LIN28B to GLUT1 immunofluorescence signal intensities showed ~2-fold increase in proliferative IH compared to propranolol treated IH samples (FIG. 3B).

To further investigate the effects of propranolol on the expression of LIN28B and let-7 in IH, the CD133+ HemSCs were used, which form hemangioma-like tumors when injected subcutaneously in immunodeficient mice[14]. First, it was tested whether HemSCs express LIN28B and the miR-498(46) cluster in NS and IH. Their expression was also tested in BeWo cells and iPSCs, which are known to express high levels of both. As negative controls, HUVECs were used that express neither LIN28B nor miR-498(46). Surprisingly, qRT-PCR revealed that compared to NS, LIN28B showed only a 2-fold increase in HemSCs, whereas in IH, iPSCs and BeWo cells LIN28B was >1000-fold (p<0.05) higher (FIG. 3C). It was found that negligible LIN28B expression was found in HUVECs (FIG. 3C). Moreover, sRNAseq analysis revealed that miR-498(46) expression levels were 3.1-, 4.1-, 28- and 492.7-fold higher in HemSCs, HUVECs, iPSCs and IH, respectively, compared to NS. Lastly, the expression of LIN28B protein in HemSC and iPSCs was also assessed by Western blot analysis, which showed negligible levels of LIN28B in HemSCs (FIG. 3D). Based on these findings, the effect of propranolol was tested in iPSCs, that express LIN28B, miR498(46) and beta-adrenergic receptors. After propranolol treatment for 72 h. iPSCs showed a 2.3-fold decrease (p<0.05) in LIN28B protein levels (FIG. 3E), but no significant differences were found at the mRNA levels (data not shown).

Propranolol Induces Mir-98(13) and Suppresses Mir-498(46) in iPSCs

To further investigate the effects of propranolol on the expression of mir-498(46) and let-7, iPSCs were treated with propranolol for 72 h and sRNAseq analysis was performed. Compared to vehicle control, propranolol treated-iPSCs showed a 3.2-fold increase in the expression of cistron mir-98(13), which encodes 9 of 12 let-7 family miRNA genes, and a 1.6-fold downregulation of mir-498(46) (Table 2). The results were confirmed by qRT-PCR, which revealed significant reduction of mir-498(46) members miR-515-5p, miR-517a, miR-518C and miR-519d and >1. 65-fold increase in let-7a expression in iPSCs treated with propranolol for 72 hr (FIG. 4A).

Propranolol Induces EMT Markers in iPSC

Figure 4:
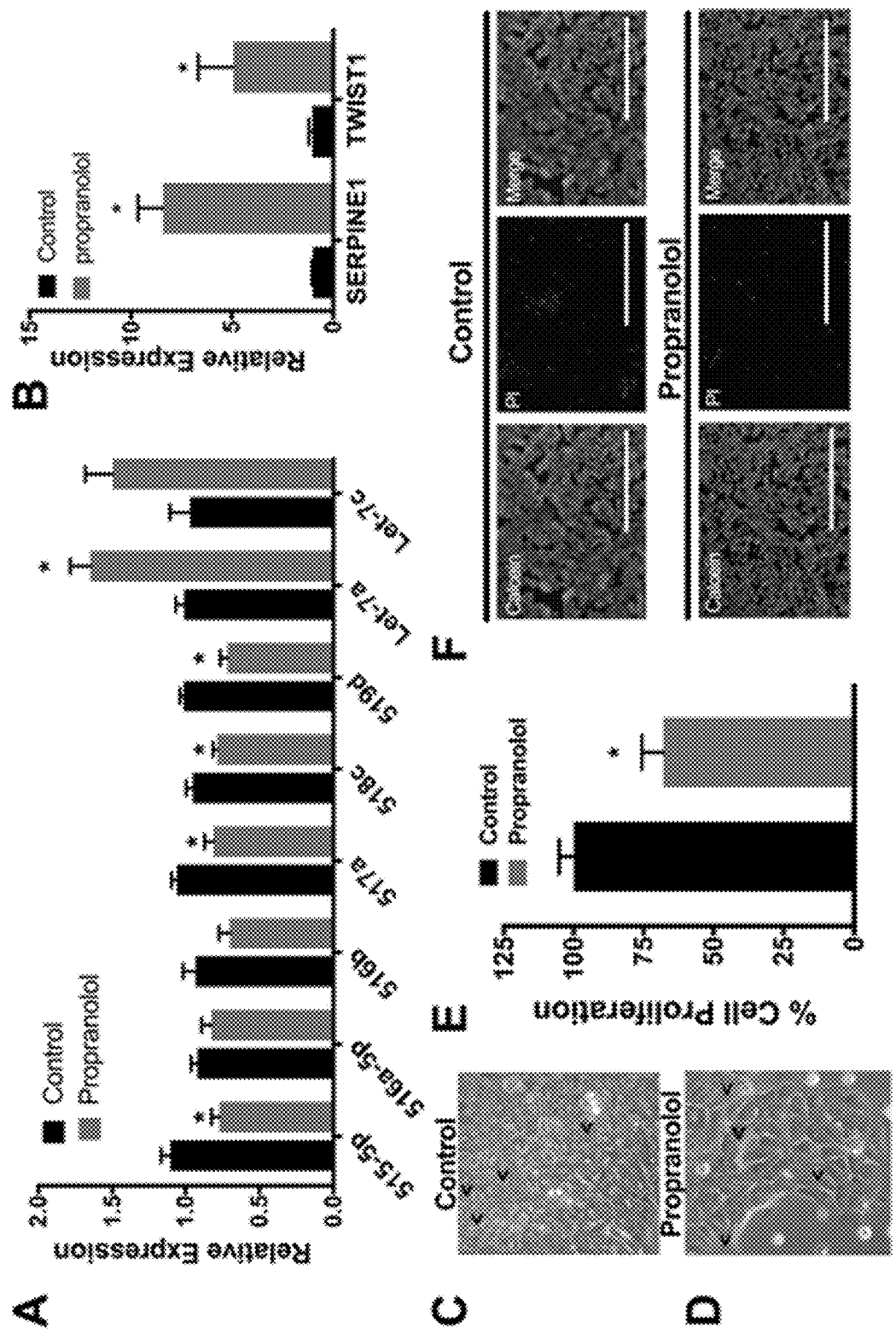
FIG. 4. Propranolol decreases the expression of mir-498 (46) cistron and induces let-7 and epithelial-mesenchymal transition (EMT) genes in iPSCs. iPSCs were treated with 50 uM propranolol or vehicle control for 72 hours. (A and B) qRT-PCR analysis of indicated miRNAs or genes normalized to U18 or GAPDH, respectively. (C and D) Representative 40× bright field images of control and propranolol-treated iPSCs. (E and F) Proliferation assay and representative fluorescence microscopy images of Calcein and propidium iodide (PI) staining for life and dead cells respectively (Scale bars: 200 µm; 20× magnification). Data represent the mean±SEM of at least 3 independent experiments. * $p<0.05$ vs. vehicle control by Student's t-test (A, B and E).

Propranolol has been shown to induce early involution of IH, during which immature vascular endothelial cells undergo EndMT, transitioning to a mesenchymal phenotype with subsequent differentiation into adipocytes[15]. To test whether propranolol induces the expression of mesenchymal markers, mRNA sequencing (RNAseq) was performed on the same propranolol and vehicle treated-iPSC samples that were used for sRNAseq. Gene set enrichment analysis performed on RNAseq data showed an enrichment of genes defining EMT (FDR 0.00046) in propranolol treated iPS cells compared to control. Gene set analysis also showed upregulation of the pathways for adipogenesis and TGF-β signaling (FDR 0.09 and 0.06 respectively). Among the most highly upregulated genes, two mesenchymal cell markers, SERPINE1 and TWIST1, showed a 12- and 2.9-fold increase (FDR $1.06 \times 10^{-6}$ and 0.004), respectively. Upregulation of SERPINE1 and TWIST1 was further confirmed by qRT-PCR, which showed 8.4- and 5-fold increased expression (p<0.05), respectively (FIG. 4B). Furthermore, gene set analysis of the RNAseq data also showed downregulation of E2F targets, G2M checkpoint and mitotic spindle pathways (FDR<0.25). Propranolol-treated iPSCs were also examined for EMT associated morphological changes and observed that propranolol treated iPSCs exhibited a more elongated cellular shape compared to control (FIGS. 4 C and D). Next, the effect of propranolol on iPSC proliferation was tested using the WST1 proliferation assay. Propranolol treatment induced a 33% decrease in cell proliferation without affecting cell viability (FIGS. 4E and F). Furthermore, gene set enrichment analysis also showed that E2F target genes and genes involved in G2/M cell cycle progression are downregulated by propranolol treatment in iPSCs (FDR 0.006 and 0.017 respectively) indicating that propranolol strongly inhibits proliferation.

Discussion

IH is a unique tumor model, characterized by a rapid proliferative phase followed by a spontaneous or propranolol-induced involution phase. The mechanisms that trigger spontaneous involution and the action of propranolol are still under investigation. The present study shows that the reprogramming factor LIN28B is highly expressed in the proliferative IH phase but is significantly decreased in involuted IH and in IH tissues from propranolol-treated patients. The high LIN28B expression in proliferative IH correlates with the expression of the ESC-enriched mir-498 (46)[44-46] and is inversely correlated with the expression of let-7 miRNAs. Treatment of iPSCs with propranolol reduced the expression of LIN28B and mir-498(46) and induced the expression of let-7 family of miRNAs and EMT genes. Moreover, propranolol treatment reduced iPSC cell proliferation.

The increase in LIN28B and reduction in let-7 reported in this study highlight the role of stem cells in the pathology of IH. Although HemSCs, which are 0.2% of the proliferative hemangioma cell population, are believed to be the cellular origin of IH, these data show that these cells do not express LIN28B and miR-498(46) in tissue culture[14, 15]. However, the in vivo data show that LIN28B is localized in GLUT1 positive endothelial cells that were previously characterized as stem cell-like[15]. These cells formed colonies that could be induced to re-differentiate into endothelial cells, pericytes/smooth muscle cells or adipocytes. Interestingly, when these GLUT1 positive endothelial cells were cultured for 3 weeks they converted to a mesenchymal phenotype and lost GLUT1 and mir-498(46) expression[7, 15]. It would be of interest to test whether freshly isolated HemSCs express LIN28B and mir-498(46) or implantation of HemSC into immunodeficient mice restores LIN28B and mir-498(46) expression. Nevertheless, increased expression of stem cell transcription factors OCT4, SOX2, NANOG and MYC have been reported in IH 6. In addition, this in vivo data also shows that in proliferative IH LIN28 was not limited to GLUT1 positive cells but was also expressed in perivascular non-endothelial cells, which are essential for the maintenance of IH vessels stability[47].

The increase in LIN28B in IH reported here may be due to transcriptional and/or post transcriptional activation. The reprogramming transcription factors such as MYC has been shown to transactivate LIN28B[48, 49]. Although little is known about the transcriptional activation of LIN28B, post-transcriptional regulation by miRNAs such as let-7 and other miRNAs has been extensively studied[23, 50]. Furthermore, LIN28B was reported to bind its own mRNA, increasing its stability and protein abundance[51]. Thus, these sRNAseq results are in line with previous reports and highlight the central role of the LIN28B/let-7 switch in governing stem cell self-renewal in the proliferative phase of IH.

It was also shown that he ESC-enriched miRNA cluster mir-498(46) is highly expressed in IH. This cluster of miRNAs is normally imprinted, with only the paternally inherited allele expressed in the placenta[30]. The overexpression of mir-498(46) seen in IH could be regulated by methylation of the upstream CpG island or by chromosomal rearrangements such as amplifications of the corresponding chromosome 19 region, as found in embryonal tumor with multilayered rosettes (ETMRs) 16, primitive neuroectodermal tumors (PNETs) and in thyroid adenomas[11, 52, 53] Given the ability of IH to undergo spontaneous involution, the elevated expression of mir-498(46) in proliferative IH is unlikely to be due to DNA amplifications or translocations, but rather, due to epigenetic modification. Thus, the previously identified promoter region and transcription start site were investigated that overlap an annotated CpG island located ~17 kb upstream of the first miRNA gene of mir-498(46). Although these findings show that, unlike NS, IH samples exhibited active transcription starting from the upstream CpG island, similar to that seen in the placenta[30], they do not preclude the existence of additional active promoter regions within mir-498(46). In fact, mir-498(46) carries numerous CpG dinucleotide islands extensively interspersed with Alu-rich repeats, which account for over 50% of the 100-kb sequence. Numerous studies showed that Alu methylation is highly dynamic and Alu-rich regions can function as independent promoters for RNA polymerase II and RNA polymerase III in both mesenchymal stem cells and cancer stem cells[44, 54, 55].

Although LIN28 is a well-established inhibitor of miRNA maturation[18, 42, 51, 56], the present study revealed that overexpression of LIN28B increased the expression of miR-516b of mir-498(46). This is especially noteworthy given that LIN28B can be used along with other reprogramming factors to generate pluripotent stem cells enriched with mir-498(46). In fact, a recent study showed that LIN28A activates gene expression by binding directly to a consensus DNA sequence at promoter regions and recruiting the CpG demethylase TET1[57]. Previous study showed that both mesenchymal stem and cancer stem cells exhibit disperse expression patterns of miRNAs of the mir-498(46) cluster rather than a bloc expression regulated by the upstream promoter[44]. Accordingly, this data shows that overexpression of LIN28B did not affect the methylation of the upstream CpG-island or increase the transcription in that region indicating the existence of downstream promoter regions. LIN28B may bind to the Alu repeats within mir-498(46), which may function as independent RNA polymerase II promoters and activate transcription by recruiting TET1. In fact, analyses of previously published PAR-CLIP data show that LIN28B binds numerous Alu repeats located in the mir-498(46)[51]. This unexpected result points to a potential binding of LIN28B to the CpG-rich Alu repeats to activate transcription. Moreover, LIN28 is a potent RNA-binding protein that regulates splicing factor abundance[58], and therefore may induce processing of the transcript of mir-498(46) cistron.

In the last decade, propranolol has become the preferred treatment for morbid proliferating IH. To date, more than 500 published articles describe the observed propranolol-induced involution of IH and the various hypotheses regarding its mechanisms of action. A new model is discussed herein through which propranolol triggers rapid IH involution. It was demonstrated that propranolol induces a shift in LIN28B/let-7 balance to favor cell differentiation and senescence. This model is based on the data presented here, which show that propranolol reduced the expression of LIN28B and increased the expression of let-7 in IH samples in vivo and in iPSCs in vitro. Furthermore, propranolol reduces the proliferation of iPSCs and initiates the conversion to mesenchymal phenotype as evidenced by the increase in SERPINE1 and TWIST1 expression, while reducing the expression of miRNAs of the mir-498(46) cistron. RNAseq and gene set analyses confirmed the downregulation in E2F targets, G2M checkpoint and mitotic spindle pathways and showed upregulation in EMT, adipogenesis, and TGF-β signaling pathways. This is the first known report to show that propranolol reduces the proliferation of iPSCs and induces EMT and adipogenesis. These profound effects of propranolol may be due in part to the reduction in LIN28B that binds and regulates mRNAs of cell cycle regulators[51] and/or as a consequence of the increase in let-7 miRNAs, which regulate Rb1/E2F genes[59]. The induction of EMT genes by propranolol is in agreement with a previous study that showed that activation of adenylyl cyclase and elevation in cAMP and EPAC signaling replaced the need for OCT4 for iPSC generation. This CAMP-dependent reprograming increased cellular division rate and induced genes involved in MET[60]. Therefore, by reducing CAMP levels, propranolol may be inducing EMT and thus accelerating IH involution. Of note, propranolol has been shown to induce adipogenesis in hemangioma stem cells[61, 62]. Lastly, the reduction in miRNAs of the mir-498(46) cistron in propranolol treated iPSCs reported here is in agreement with previous work that showed that propranolol treated IH tissues contained significantly lower levels of mir-498(46) miRNAs than did proliferative, untreated IH[7].

The LIN28/let-7 axis is implicated not only in pluripotency but also in tumorigenesis, especially in cancer stem cells, which are resistant to chemotherapies and promote metastasis[50, 63] In fact, numerous pre-clinical and clinical studies provide evidence that propranolol increases chemosensitivity and reduces the metastatic rates in multiple cancer types[64]. The present work shows the role of the LIN28B/let-7 switch in IH pathogenesis and propranolol induced IH involution. This study also provides new therapeutic methods for detecting and treating tumors and cancers in which the LIN28/let-7 pathway is imbalanced.

Material and Methods
Tissue Specimens

Institutional review board approval for collection of resected human hemangiomas was obtained from Columbia University College of Physicians and Surgeons (IRB #AAAA9976). Term placental tissues from normotensive patients who were delivered by cesarean section were obtained from Tampa General Hospital/University of South Florida (IRB #00015578). Written informed consent was obtained from all patients. De-identified foreskin was used as normal infant skin (NS) and obtained from Tampa General Hospital, Tampa Florida.

Cell Culture

The human iPSC line SCVI274 was a gift from Dr Joseph C. Wu at Stanford Cardiovascular Institute, Stanford University School of Medicine. iPSCs were cultured on matrigel coated 6-well plates and maintained in Essential 8 medium (A1517001, Life Technologies) and passaged every fourth day. HEK293 cells (Life Technologies) were maintained in DMEM Supplemented with 10% heat-inactivated fetal bovine serum (Sigma-Aldrich). Propranolol (Sigma-Aldrich, P0884) was reconstituted in DMSO and used at 50 µM concentration for all experiments. The HemSC line H42 was a gift from Dr. June Wu at the Department of Surgery, Columbia University College of Physicians and Surgeons. Briefly, freshly dissected IH tissues were digested in 0.2% collagenase A (Roche Diagnostics, Indianapolis, IN). Suspension of single cells were selected using anti-CD133-coated magnetic beads (Miltenyi Biotec) and cultured on fibronectin-coated (1 µg/cm$^2$) plates with endothelial growth media-2 SingleQuot (EBM-2, CC-3156; Cambrex) Supplemented with 20% FBS[27, 28]. HemSCs were maintained in EBM-2 SingleQuot media Supplemented with 20% FBS.

Transient Transfection

For LIN28B over-expression experiments, $10^5$ HEK293 cells per ml were seeded in 12-well plates (Greiner Bio). The following day, the cells were transfected with pcDNA3-FLAG-Lin28B, a gift from Narry Kim (Addgene plasmid #51373) using Lipofectamine 2000 (Life Technologies) according to the manufacturer's instructions. The culture medium was changed 24 hours after transfection and total RNA was harvested at 72 hours.

Cell Proliferation iPSCs were grown in 6 well plates and split 1:10 at 3-day intervals. Cells were seeded at subconfluency on a matrigel-coated 96-well plate in Essential 8 media then treated with 50 µM propranolol or vehicle control for 72 hours. WST1 proliferation assays were performed as previously described[29].

Cell Viability

The viability of iPSCs after propranolol treatment was analyzed by staining of live and dead cells with calcein AM and Propidium iodide (PI), respectively, 72 hours after treatment. Cells were washed with PBS before the addition of 2 µM calcein AM and 4 µM PI solution. Fluorescence microscopy images were captured after 15 minutes.

RNA Isolation, RT-PCR and Quantitative PCR (qPCR)

Total RNA was isolated from human tissues and cultured cells using an RNeasy Mini Kit (Qiagen) and stored at −80° ° C. in RNAse-free water. For RT-PCR analysis, 1 µg total RNA was reverse transcribed using random hexamer or oligodT primers and M-MuLV reverse transcriptase (New England Biolabs) according to the manufacturer's specifications.

For transcription assessments, cDNA products were amplified for 25 PCR cycles using previously described P0, P1, P5, P8 and P9 primer sets[30] and Q5 High Fidelity DNA polymerase (New England Biolabs). PCR products were run on 1% agarose gels and imaged with a BioDoc-It imaging system (UVP). All primers used in this study were obtained from Sigma Aldrich. To assess relative mRNA and miRNA expression levels, quantitative PCR (qRT-PCR) of cDNA products was performed using the following ThermoFisher TaqMan qRT-PCR probes: LIN28A (Hs00702808_s1), LIN28B (Hs01013729_m1), SERPINE1 (Hs00167155_m1), TWIST1 (Hs01675818_s1), GAPDH (Hs02786624_g1) miR-515-5p (001112), miR-516a-5p (002416), miR-516b (001150), miR-517a (002402), miR-518c (002401), miR-519d (002403), let-7a (000377), let-7c (000379), U18 (001204). Taqman probes were used according to manufacturer's instructions with TaqMan Fast Advanced Master Mix and QuantStudio 3 instrument (Life Technologies) as previously described[31]. Data were analyzed by the $\Delta\Delta C_t$ method: target $C_t$ values and were normalized to GAPDH $C_t$ values.

DNA Isolation and HpaII Sensitivity Assay

DNA was isolated from cultured cells using the Blood and Tissue Kit (Qiagen) and stored at −20° C. in RNAse-free water. 300 ng of DNA was digested with 2 µl of 10,000 units/ml HpaII (NEB) restriction enzyme or water (mock) for 12 hours. qPCR was performed using 60 ng of DNA from mock or HpaII reactions with primers designed to amplify 340 bp region containing 6 HpaII restriction sites in the C19MC CpG island (F: 5'-GCGCCGGCTGCACGTCCCT-TAGGAG (SEQ ID NO:1) and R:5'-CCCGCTGCCTG-GAAGTATCGCCACC (SEQ ID NO:2)) and SYBR Green (SYBR Green PCR Master mix, Bio-Rad) in a QuantStudio 3 instrument (Applied Biosystems). HpaII sensitivity was calculated using the formula $[1-2^{Ct(mock)-Ct(HpaII)}]\times 100\%$ as described[32].

Immunofluorescence

Paraffin embedded infantile hemangioma and placenta sections (10 µm) were immunostained with primary antibodies against LIN28B 40 ug/ml (Abcam Cat #ab71415, RRID:AB_2135050) and GLUT1 3.4 ug/ml (Abcam Cat #ab40084, RRID:AB_2190927) overnight at 4° C. Sections were washed 3 times in PBS and incubated with 4 ug/ml secondary antibody Alexa Fluor 488 (Life Technologies Cat #a21202, RRID:AB_141607) for GLUT1 and alexa fluor cy3 (Life Technologies Cat #a10520, RRID:AB_2534029) for LIN28B for 30 minutes at room temperature. The sections were then washed with PBS and mounted with ProLong Diamond Antifade Mountant with DAPI, (Invitogen). Confocal images were obtained using an Olympus FV 1200 instrument. Immunofluorescence intensities were measured using ImageJ software as described[33]. Fluorescence intensities were normalized to background intensities of secondary antibody only controls.

Immunoblotting

Immunoblot analyses were performed as previously described[34] using 24 ng/ml antibodies against GAPDH (Cell Signaling Technology Cat #2118L RRID:AB_561053), 0.2 µg/µl antibodies against LIN28B (Abcam Cat #ab71415 RRID:AB_2135050) followed by IRDye 680 donkey anti-rabbit IGG secondary antibodies (0.2 µg/ml, LI-COR, 926-68073 RRID: AB_10954442). Immunoblots were imaged using the Odyssey Infrared Imaging System (LI-COR) and quantified using Image Studio software (LI-COR).

miRNA- and mRNA-Sequencing

Two µg of total RNA were converted into a small-RNA cDNA library according to the previously published protocol[35]. Briefly, the RNA input for each sample was ligated to a 3' adaptor barcoded sequence, pooled, size selected and gel purified, followed by 5' adapter ligation and then subjected to size selection and gel purification. The cDNA library preparation was completed by second strand synthesis using SuperScript III, alkaline RNA hydrolysis, and PCR amplification for 10 cycles. mRNA libraries were prepared by utilizing the Illumina TruSeq Stranded mRNA LT protocol using 500 ng total RNA and NEB's Protoscript II reverse transcriptase for the first-strand cDNA synthesis according to the manufacturer's protocol. Individual RNAseq libraries were quality controlled on an Agilent TapeStation with a High Sensitivity D1000 ScreenTape. Indexed samples were quantified using the Qubit dsDNA HS assay and pooled at equimolar concentration (10 nM). The libraries were sequenced on an Illumina NextSeq 500 sequencer 75-bp paired-end in mid-output mode in the Genomics Core Facility of The Rockefeller University.

Bioinformatics Analysis

The miRNA read annotation for sRNAseq experiments was performed as previously described[36,37] using an slightly updated, manually curated miRNA reference based on previous work 38. For nomenclature of single miRNAs and definition and nomenclature of miRNA cistrons (or "precursor clusters") see FIG. S1 of Akat et al.[39]. The RNAseq data was aligned to the Human Genome Build 38 using the STAR aligner[40] (version 2.0.4j) allowing for two mismatches. Expression values (count matrices) were generated using featureCounts against gene definitions from Ensembl release 88 (GTF file) using fractional counting of multi-mapping reads.

Statistical Analysis sRNAseq and RNAseq data analyses were performed using the R statistical language. Differential analysis was performed using the Bioconductor package edgeR. All RT-PCR and immunoblotting data are reported as mean±standard error of the mean (SEM). All data were tested for normality. Comparisons between two groups of normally distributed data were made by two-tailed Student's t-tests with correction for unequal variance, while comparisons of data that was not normally distributed were done using Mann-Whitney U tests. Comparisons with more than two groups were subject to one-way ANOVA with Dunnett's post hoc tests against controls. Statistical testing was performed with IBM SPSS 24. $P<0.05$ was considered statistically significant or as specified in the relevant tables and figure legends.

TABLE 1

Expression differences of highly expressed miRNA cistrons in IH vs. NS by sRNAseq. Highly expressed cistrons were defined as being within the top 90% RNAseq reads in any of the 8 IH and 5 NS samples. Shown are cistrons with a false discovery rate of less than 25% in the differential analysis.

| Cistron (mir-) | Normalized frequency (%) | | Fold change | P Value | FDR |
|---|---|---|---|---|---|
| | Infantile hemangioma | Normal skin | | | |
| 498(46) | 8.888 | 0.018 | 492.7 | 3.99E−12 | 1.27E−09 |
| 195(2) | 2.312 | 0.543 | 4.3 | 3.65E−05 | 4.29E−04 |
| 378(1) | 3.760 | 0.899 | 4.2 | 1.25E−05 | 1.80E−04 |
| 140(1) | 1.079 | 0.279 | 3.9 | 1.76E−04 | 1.66E−03 |
| 30a(4) | 5.075 | 1.473 | 3.4 | 9.02E−05 | 9.22E−04 |
| 10b(1) | 2.428 | 0.724 | 3.4 | 5.04E−02 | 1.49E−01 |
| 15a(4) | 1.576 | 0.523 | 3.0 | 7.01E−03 | 3.27E−02 |
| 142(1) | 0.536 | 0.195 | 2.8 | 9.35E−03 | 4.11E−02 |
| 29a(4) | 1.902 | 0.698 | 2.7 | 3.17E−02 | 1.06E−01 |
| 181a-1(4) | 1.570 | 0.596 | 2.6 | 7.35E−04 | 5.98E−03 |
| 424(2) | 3.495 | 1.437 | 2.4 | 3.05E−03 | 1.90E−02 |
| 26a-1(2) | 9.431 | 3.934 | 2.4 | 1.94E−02 | 7.49E−02 |
| 22(1) | 3.401 | 1.420 | 2.4 | 1.30E−02 | 5.43E−02 |
| 144(2) | 3.972 | 1.679 | 2.4 | 6.92E−02 | 1.91E−01 |
| 143(2) | 18.461 | 9.717 | 1.9 | 8.68E−02 | 2.24E−01 |
| 21(1) | 4.601 | 2.758 | 1.7 | 3.72E−02 | 1.22E−01 |
| 26b(1) | 1.467 | 0.901 | 1.6 | 7.79E−02 | 2.06E−01 |
| 191(2) | 0.675 | 0.438 | 1.5 | 1.17E−02 | 4.99E−02 |
| 126(1) | 1.724 | 1.103 | 1.6 | 8.90E−02 | 2.27E−01 |
| 30b(2) | 0.970 | 0.640 | 1.5 | 6.42E−02 | 1.80E−01 |

TABLE 1-continued

Expression differences of highly expressed miRNA cistrons in IH vs. NS by sRNAseq. Highly expressed cistrons were defined as being within the top 90% RNAseq reads in any of the 8 IH and 5 NS samples. Shown are cistrons with a false discovery rate of less than 25% in the differential analysis.

| Cistron (mir-) | Normalized frequency (%) | | Fold change | P Value | FDR |
|---|---|---|---|---|---|
| | Infantile hemangioma | Normal skin | | | |
| 25(3) | 0.988 | 0.706 | 1.4 | 8.19E-02 | 2.13E-01 |
| 135a-1(3) | 0.764 | 1.097 | -1.4 | 7.29E-02 | 1.96E-01 |
| 17(12) | 1.145 | 1.754 | -1.5 | 4.18E-02 | 1.32E-01 |
| 130a(1) | 0.299 | 0.501 | -1.7 | 3.72E-02 | 1.22E-01 |
| 199b(1) | 0.785 | 1.437 | -1.8 | 2.66E-02 | 9.59E-02 |
| 148a(1) | 0.993 | 4.427 | -4.5 | 1.39E-06 | 2.45E-05 |
| 221(2) | 0.226 | 1.130 | -5.0 | 2.08E-09 | 1.65E-07 |
| 210(1) | 0.025 | 0.376 | -14.9 | 1.40E-08 | 6.34E-07 |
| 141(2) | 0.049 | 1.947 | -40.8 | 6.17E-06 | 9.31E-05 |
| 200a(3) | 0.010 | 0.553 | -58.5 | 6.34E-08 | 1.78E-06 |
| 203(1) | 0.014 | 6.200 | -461.0 | 1.69E-10 | 7.56E-09 |
| 205(1) | 0.013 | 1.730 | -150.3 | 1.14E-07 | 2.59E-06 |

TABLE 2

Propranolol treatment decreases miR-498(46) expression and increases let-7 miRNA expression in iPSCs. Shown are all cistrons with and FDR <25%. In bold mir-498(46) and mir-98(13).

| Cistron (mir-) | Normalized frequency (%) | | Fold change | P Value | FDR |
|---|---|---|---|---|---|
| | Propranolol | Control | | | |
| 1226(1) | 0 | 0.0029 | -579.2 | 0.0004 | 0.0994 |
| 33b(1) | 0.002 | 0.0087 | -4.3 | 0.0094 | 0.2276 |
| 488(1) | 0.0022 | 0.0082 | -3.8 | 0.0024 | 0.1167 |
| 498(46) | 0.4075 | 0.6333 | -1.6 | 0.0021 | 0.1167 |
| 21(1) | 10.5844 | 6.864 | 1.5 | 0.002 | 0.1167 |
| 188(8) | 0.1459 | 0.0842 | 1.7 | 0.0063 | 0.2276 |
| 98(13) | 0.2313 | 0.0836 | 2.8 | 0.0074 | 0.2276 |
| 10b(1) | 0.0176 | 0.0024 | 7.5 | 0.0086 | 0.2276 |
| 10a(1) | 0.0168 | 0.0001 | 120.8 | 0.0018 | 0.1167 |
| 3155(1) | 0.0014 | 0 | 284.3 | 0.0086 | 0.2276 |

Abbreviations
  C19MC Chromosome 19 miRNA cluster
  EMT Epithelial to mesenchymal transition
  EndMT Endothelial to mesenchymal transition
  ESC Embryonic stem cells
  HemSC Hemangioma stem cell
  IH Infantile hemangioma
  iPSC Induced Pluripotent Stem Cells
  MET Mesenchymal to epithelial transition
  NS Normal skin References Cited in this Example
1. Smith C J, Friedlander S F, Guma M, Kavanaugh A, Chambers C D. Infantile hemangiomas: An updated review on risk factors, pathogenesis, and treatment. *Birth Defects Res.* 2017; 109:809-815
2. Darrow D H, Greene A K, Mancini A J, Nopper A J, Section On Dermatology SOO-H, Neck S, Section On Plastic S. Diagnosis and management of infantile hemangioma: Executive summary. *Pediatrics.* 2015; 136:786-791
3. Greenberger S, Bischoff J. Pathogenesis of infantile haemangioma. *Br J Dermatol.* 2013; 169:12-19
4. North P E, Waner M, Mizeracki A, Mihm M C, Jr. Glut1: A newly discovered immunohistochemical marker for juvenile hemangiomas. *Hum Pathol.* 2000; 31:11-22
5. Mulliken J B, Glowacki J. Hemangiomas and vascular malformations in infants and children: A classification based on endothelial characteristics. *Plast Reconstr Surg.* 1982; 69:412-422
6. Amaya C N, Bryan B A. Enrichment of the embryonic stem cell reprogramming factors oct4, nanog, myc, and sox2 in benign and malignant vascular tumors. *BMC Clin Pathol.* 2015; 15:18
7. Strub G M, Kirsh A L, Whipple M E, Kuo W P, Keller R B, Kapur R P, Majesky M W, Perkins J A. Endothelial and circulating c19mc micrornas are biomarkers of infantile hemangioma. *JCI Insight.* 2016; 1:e88856
8. Bentwich I, Avniel A, Karov Y, Aharonov R, Gilad S, Barad O, Barzilai A, Einat P, Einav U, Meiri E, Sharon E, Spector Y, Bentwich Z. Identification of hundreds of conserved and nonconserved human micrornas. *Nat Genet.* 2005; 37:766-770
9. Kleinman C L, Gerges N, Papillon-Cavanagh S et. al. Fusion of ttyh1 with the c19mc microrna cluster drives expression of a brain-specific dnmt3b isoform in the embryonal brain tumor etmr. *Nat Genet.* 2014; 46:39-44
10. Morales-Prieto D M, Ospina-Prieto S, Chaiwangyen W, Schoenleben M, Markert U R. Pregnancy-associated mirna-clusters. *J Reprod Immunol.* 2013; 97:51-61
11. Li M, Lee K F, Lu Y, Clarke I et. al. Frequent amplification of a chr19q13.41 microrna polycistron in aggressive primitive neuroectodermal brain tumors. *Cancer Cell.* 2009; 16:533-546
12. Barnes C M, Huang S, Kaipainen A, Sanoudou D, Chen E J, Eichler G S, Guo Y, Yu Y, Ingber D E, Mulliken J B, Beggs A H, Folkman J, Fishman S J. Evidence by molecular profiling for a placental origin of infantile hemangioma. *Proc Natl Acad Sci USA.* 2005; 102:19097-19102
13. North P E, Waner M, Mizeracki A, Mrak R E, Nicholas R, Kincannon J, Suen J Y, Mihm M C, Jr. A unique microvascular phenotype shared by juvenile hemangiomas and human placenta. *Arch Dermatol.* 2001; 137:559-570
14. Khan Z A, Boscolo E, Picard A, Psutka S, Melero-Martin J M, Bartch T C, Mulliken J B, Bischoff J. Multipotential stem cells recapitulate human infantile hemangioma in immunodeficient mice. *J Clin Invest.* 2008; 118:2592-2599

15. Huang L, Nakayama H, Klagsbrun M, Mulliken J B, Bischoff J. Glucose transporter 1-positive endothelial cells in infantile hemangioma exhibit features of facultative stem cells. *Stem Cells*. 2015; 33:133-145
16. Leaute-Labreze C. Dumas de la Roque E, Hubiche T, Boralevi F, Thambo J B, Taieb A. Propranolol for severe hemangiomas of infancy. *N Engl J Med*. 2008; 358:2649-2651
17. Leaute-Labreze C. Hoeger P. Mazereeuw-Hautier J, et. al. A randomized, controlled trial of oral propranolol in infantile hemangioma. *N Engl J Med*. 2015; 372:735-746
18. Heo I, Joo C. Cho J, Ha M, Han J, Kim V N. Lin28 mediates the terminal uridylation of let-7 precursor microrna. *Mol Cell*. 2008; 32:276-284
19. Viswanathan S R. Daley G Q, Gregory R I. Selective blockade of microrna processing by lin28. *Science*. 2008; 320:97-100
20. Reinhart B J, Slack F J, Basson M, Pasquinelli A E, Bettinger J C, Rougvie A E, Horvitz H R, Ruvkun G. The 21-nucleotide let-7 rna regulates developmental timing in *Caenorhabditis elegans*. *Nature*. 2000; 403:901-906
21. Takahashi K. Yamanaka S. Induction of pluripotent stem cells from mouse embryonic and adult fibroblast cultures by defined factors. *Cell*. 2006; 126:663-676
22. Yu J. Vodyanik M A, Smuga-Otto K. Antosiewicz-Bourget J, Frane J L, Tian S, Nie J, Jonsdottir G A. Ruotti V. Stewart R, Slukvin, I I, Thomson J A. Induced pluripotent stem cell lines derived from human somatic cells. *Science*. 2007; 318:1917-1920
23. Zhang J. Ratanasirintrawoot S, Chandrasekaran S, et. al. Lin28 regulates stem cell metabolism and conversion to primed pluripotency. *Cell Stem Cell*. 2016; 19:66-80
24. Kalluri R. Weinberg R A. The basics of epithelial-mesenchymal transition. *J Clin Invest*. 2009; 119:1420-1428
25. Gonzalez D M, Medici D. Signaling mechanisms of the epithelial-mesenchymal transition. *Science Signaling*. 2014; 7
26. Li R H, Liang J L, Ni S. Zhou T, et. al. A mesenchymal-to-epithelial transition initiates and is required for the nuclear reprogramming of mouse fibroblasts. *Cell Stem Cell*. 2010; 7:51-63
27. Munabi N C, England R W, Edwards A K, Kitajewski A A, Tan Q K, Weinstein A, Kung J E, Wilcox M, Kitajewski J K. Shawber C J, Wu J K. Propranolol targets hemangioma stem cells via camp and mitogen-activated protein kinase regulation. *Stem Cells Transl Med*. 2016; 5:45-55
28. Khan Z A, Melero-Martin J M, Wu X, Paruchuri S. Boscolo E. Mulliken J B, Bischoff J. Endothelial progenitor cells from infantile hemangioma and umbilical cord blood display unique cellular responses to endostatin. *Blood*. 2006; 108:915-921
29. Santulli G, Wronska A, Uryu K, Diacovo T G, Gao M, Marx S O, Kitajewski J, Chilton J M, Akat K M, Tuschl T, Marks A R, Totary-Jain H. A selective microrna-based strategy inhibits restenosis while preserving endothelial function. *J Clin Invest*. 2014; 124:4102-4114
30. Noguer-Dance M. Abu-Amero S, Al-Khtib M, Lefevre A, Coullin P. Moore G E, Cavaille J. The primate-specific microrna gene cluster (c19mc) is imprinted in the placenta. *Hum Mol Genet*. 2010; 19:3566-3582
31. Totary-Jain H, Sanoudou D, Ben-Dov I Z, Dautriche C N, Guarnieri P. Marx S O, Tuschl T, Marks A R. Reprogramming of the microrna transcriptome mediates resistance to rapamycin. *J Biol Chem*. 2013; 288:6034-6044
32. Guo J U, Su Y, Zhong C. Ming G L, Song H. Hydroxylation of 5-methylcytosine by tet1 promotes active DNA demethylation in the adult brain. *Cell*. 2011; 145:423-434
33. Jensen E C. Quantitative analysis of histological staining and fluorescence using imagej. *Anatomical Record-Advances in Integrative Anatomy and Evolutionary Biology*. 2013; 296:378-381
34. Totary-Jain H, Sanoudou D, Dautriche C N, Schneller H, Zambrana L, Marks A R. Rapamycin resistance is linked to defective regulation of skp2. *Cancer Res*. 2012; 72:1836-1843
35. Hafner M, Renwick N, Farazi T A, Mihailovic A, Pena J T, Tuschl T. Barcoded cdna library preparation for small rna profiling by next-generation sequencing. *Methods*. 2012; 58:164-170
36. Farazi T A, Brown M, Morozov P. Ten Hoeve J J, Ben-Dov I Z, Hovestadt V, Hafner M, Renwick N, Mihailovic A, Wessels L F, Tuschl T. Bioinformatic analysis of barcoded cdna libraries for small rna profiling by next-generation sequencing. *Methods*. 2012; 58:171-187
37. Brown M, Suryawanshi H, Hafner M, Farazi T A, Tuschl T. Mammalian mirna curation through next-generation sequencing. *Front Genet*. 2013; 4:145
38. Farazi T A, Horlings H M, Ten Hoeve J J, et. al. Microrna sequence and expression analysis in breast tumors by deep sequencing. *Cancer Res*. 2011; 71:4443-4453
39. Akat K M, Moore-McGriff D, Morozova P. Browna M, Gogakos T, Da Rosa J C. Mihailovic A, Sauer M, Ji R P, Ramarathnam A, Totary-Jain H, Williams Z. Tuschl T, Schulze P C. Comparative rna-sequencing analysis of myocardial and circulating small rnas in human heart failure and their utility as biomarkers. *Proceedings of the National Academy of Sciences of the United States of America*. 2014; 111:11151-11156
40. Dobin A, Davis C A, Schlesinger F, Drenkow J, Zaleski C, Jha S, Batut P. Chaisson M, Gingeras T R. Star: Ultrafast universal rna-seq aligner. *Bioinformatics*. 2013; 29:15-21
41. Harbi S. Wang R. Gregory M, Hanson N, Kobylarz K. Ryan K. Deng Y, Lopez P, Chiriboga L, Mignatti P. Infantile hemangioma originates from a dysregulated but not fully transformed multipotent stem cell. *Sci Rep*. 2016; 6:35811
42. Heo I, Joo C, Kim Y K, Ha M, Yoon M J, Cho J, Yeom K H, Han J, Kim V N. Tut4 in concert with lin28 suppresses microrna biogenesis through pre-microrna uridylation. *Cell*. 2009; 138:696-708
43. Rybak A, Fuchs H, Smirnova L, Brandt C, Pohl E E, Nitsch R, Wulczyn F G. A feedback loop comprising lin-28 and let-7 controls pre-let-7 maturation during neural stem-cell commitment. *Nat Cell Biol*. 2008; 10:987-993
44. Nguyen P N, Huang C J, Sugii S, Cheong S K, Choo K B. Selective activation of mirnas of the primate-specific chromosome 19 mirna cluster (c19mc) in cancer and stem cells and possible contribution to regulation of apoptosis. *J Biomed Sci*. 2017; 24:20
45. Laurent L C, Chen J, Ulitsky I, Mueller F J, Lu C, Shamir R. Fan J B, Loring J F. Comprehensive microrna profiling reveals a unique human embryonic stem cell signature dominated by a single seed sequence. *Stem cells*. 2008; 26:1506-1516
46. Bar M, Wyman S K, Fritz B R, et. al. Microrna discovery and profiling in human embryonic stem cells by deep sequencing of small rna libraries. *Stem cells*. 2008; 26:2496-2505

47. Edwards A K, Glithero K, Grzesik P, Kitajewski A A, Munabi N C, Hardy K, Tan Q K, Schonning M, Kangsamaksin T, Kitajewski J K, Shawber C J, Wu J K. Notch3 regulates stem-to-mural cell differentiation in infantile hemangioma. *JCI Insight.* 2017; 2
48. Cotterman R, Knoepfler P S. N-myc regulates expression of pluripotency genes in neuroblastoma including lif, klf2, klf4, and lin28b. *PLOS One.* 2009; 4:e5799
49. Beckers A, Van Peer G, Carter D R, et. al. Mycn-driven regulatory mechanisms controlling lin28b in neuroblastoma. *Cancer Lett.* 2015; 366:123-132
50. Shyh-Chang N, Daley G Q. Lin28: Primal regulator of growth and metabolism in stem cells. *Cell Stem Cell.* 2013; 12:395-406
51. Hafner M, Max K E, Bandaru P, Morozov P, Gerstberger S, Brown M, Molina H, Tuschl T. Identification of mrnas bound and regulated by human lin28 proteins and molecular requirements for rna recognition. *RNA.* 2013; 19:613-626
52. Louis D N, Perry A, Reifenberger G, von Deimling A, Figarella-Branger D, Cavenee W K, Ohgaki H, Wiestler O D, Kleihues P, Ellison D W. The 2016 world health organization classification of tumors of the central nervous system: A summary. *Acta Neuropathol.* 2016; 131: 803-820
53. Rippe V, Dittberner L, Lorenz V N, Drieschner N, Nimzyk R, Sendt W, Junker K, Belge G, Bullerdiek J. The two stem cell microrna gene clusters c19mc and mir-371-3 are activated by specific chromosomal rearrangements in a subgroup of thyroid adenomas. *PLOS One.* 2010; 5:e9485
54. Borchert G M, Lanier W, Davidson B L. Rna polymerase iii transcribes human micrornas. *Nat Struct Mol Biol.* 2006; 13:1097-1101
55. Saito Y, Suzuki H, Tsugawa H, Nakagawa I, Matsuzaki J, Kanai Y, Hibi T. Chromatin remodeling at alu repeats by epigenetic treatment activates silenced microrna-512-5p with downregulation of mcl-1 in human gastric cancer cells. *Oncogene.* 2009; 28:2738-2744
56. Piskounova E, Polytarchou C, Thornton J E, LaPierre R J, Pothoulakis C, Hagan J P, Iliopoulos D, Gregory R I. Lin28a and lin28b inhibit let-7 microrna biogenesis by distinct mechanisms. *Cell.* 2011; 147:1066-1079
57. Zeng Y, Yao B, Shin J, et. al. Lin28a binds active promoters and recruits tet1 to regulate gene expression. *Mol Cell.* 2016; 61:153-160
58. Wilbert M L, Huelga S C, Kapeli K, et. al. Lin28 binds messenger rnas at ggaga motifs and regulates splicing factor abundance. *Mol Cell.* 2012; 48:195-206
59. Benhamed M, Herbig U, Ye T, Dejean A, Bischof O. Senescence is an endogenous trigger for microrna-directed transcriptional gene silencing in human cells. *Nat Cell Biol.* 2012; 14:266-275
60. Fritz A L, Adil M M, Mao S R, Schaffer D V. Camp and epac signaling functionally replace oct4 during induced pluripotent stem cell reprogramming. *Mol Ther.* 2015; 23:952-963
61. England R W, Hardy K L, Kitajewski A M, Wong A, Kitajewski J K, Shawber C J, Wu J K. Propranolol promotes accelerated and dysregulated adipogenesis in hemangioma stem cells. *Ann Plast Surg.* 2014; 73 Suppl 1:S119-124
62. Ma X, Zhao T, Ouyang T, Xin S, Ma Y, Chang M. Propranolol enhanced adipogenesis instead of induction of apoptosis of hemangiomas stem cells. *Int J Clin Exp Pathol.* 2014; 7:3809-3817
63. Balzeau J, Menezes M R, Cao S, Hagan J P. The lin28/let-7 pathway in cancer. *Front Genet.* 2017; 8:31
64. Pantziarka P, Bouche G, Sukhatme V, Meheus L, Rooman I, Sukhatme V P. Repurposing drugs in oncology (redo)-propranolol as an anti-cancer agent. *Ecancermedicalscience.* 2016; 10:680

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

I claim:

1. A method of treating a subject having a tumor, comprising:
   a) obtaining a biological sample derived from the subject having a tumor;
   b) quantifying an expression level of a biomarker in the biological sample derived from the subject relative to a reference control, wherein the biomarker consists of LIN28B, wherein the reference control is an expression level of the biomarker from a subject without a tumor or a cancer;
   c) determining the tumor as responsive to propranolol treatment if the expression level of the biomarker LIN28B is higher in the biological sample derived from the subject compared to the reference control; and
   d) administering a therapeutically effective amount of propranolol to the subject determined to have the tumor that is responsive to propranolol in c).

2. The method of claim 1, wherein the biological sample comprises one or a combination of biopsy tissue, tumor cells, or a blood sample.

3. The method of claim 1, wherein the quantifying is carried out by one or a combination of Polymerase Chain Reaction, Real Time-Polymerase Chain Reaction, Real Time Reverse Transcriptase-Polymerase Chain Reaction, and Real-time quantitative RT-PCR, Northern blot analysis, in situ hybridization, and probe array.

4. The method of claim 1, wherein the tumor is a cancer.

5. The method of claim 4, wherein the cancer is selected from a brain cancer, breast cancer, or cervical cancer.

6. The method of claim 5, wherein the cancer is a brain cancer.

7. The method of claim 1, wherein the subject is a human.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
gcgccggctg cacgtccctt aggag                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
cccgctgcct ggaagtatcg ccacc                                          25